United States Patent
Floyd

(10) Patent No.: US 7,271,008 B2
(45) Date of Patent: Sep. 18, 2007

(54) QUALITY CONTROL OF ASSAYS

(76) Inventor: Alton David Floyd, 23126 S. Shore Dr., Edwardsburg, MI (US) 49112

( * ) Notice: Subject to any disclaimer, the term of this patent is extended or adjusted under 35 U.S.C. 154(b) by 644 days.

(21) Appl. No.: 10/619,735

(22) Filed: Jul. 15, 2003

(65) Prior Publication Data

US 2004/0016035 A1 Jan. 22, 2004

Related U.S. Application Data

(60) Provisional application No. 60/396,198, filed on Jul. 15, 2002.

(51) Int. Cl.
*G01N 33/543* (2006.01)
(52) U.S. Cl. .................. 436/518; 436/524; 436/528; 436/529; 436/527; 436/164; 435/283.1; 435/287.1; 435/287.2; 435/288.3; 435/288.7; 422/50; 422/61; 422/68.1; 422/82.05
(58) Field of Classification Search ................ 436/518, 436/524, 528, 529, 527, 164; 435/4, 7.1, 435/283.1, 287.1, 287.2, 288.3, 288.7; 422/50, 422/61, 68.1, 82.05
See application file for complete search history.

(56) References Cited

U.S. PATENT DOCUMENTS 4,683,203 A 7/1987 Anton et al.
5,143,714 A * 9/1992 Cosgrove et al. ............ 435/7.1
6,281,004 B1 8/2001 Bogen et al.

OTHER PUBLICATIONS

Klebe, R..J., "Cytoscribing: a method for micropositioning cells and the construction of two- and three-dimensional synthetic tissues," *Exp. Cell Res.* 179:362-373 (1988).
Sompuram, S.R. et al., "A novel quality control slide for quantitative immunohistochemistry testing," *J. Histochem. Cytochem.* 50:1425-1434 (2002).
van der Ploeg, M. et al., "Matrix models. Essential tools for microscopic cytochemical research," *Histochemistry* 84:283-300 (1986).
Wittekind et al., "On the nature of Romanowsky-Giemsa staining and the Romanowsky-Giemsa effect. I. Model experiments on the specificity of azure B-eosin Y stain as compared with other thiazine dye-eosin Y combinations," *Histochem. J.* 17:263-289 (1985).

* cited by examiner

*Primary Examiner*—Long V. Le
*Assistant Examiner*—Melanie J. Yu
(74) *Attorney, Agent, or Firm*—Yi Li

(57) ABSTRACT

The invention relates to a device and methods for determining the quality of reagents used in an assay process, particularly a multistep immunohistochemical assay. In particular, the device comprises a substrate with a plurality of compounds affixed to a substrate, where each compound is reactive with a reagent used in the assay.

16 Claims, 2 Drawing Sheets

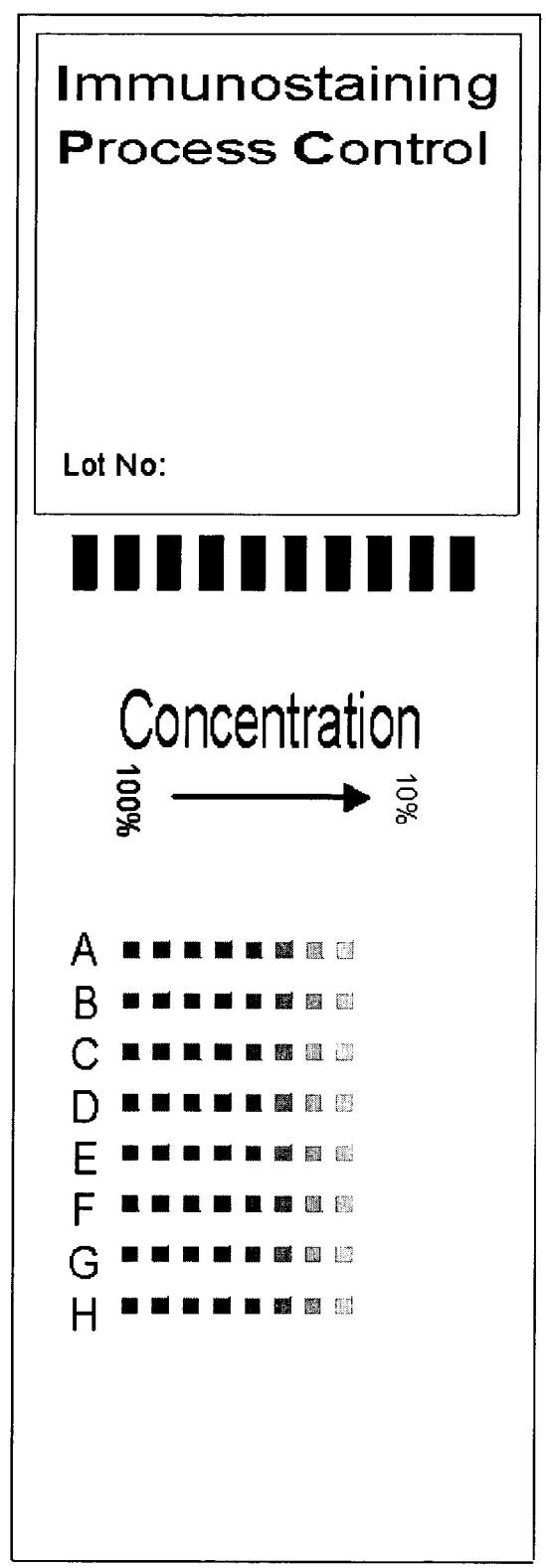
*FIG_1*

Immunostaining Process Control Slide Specification
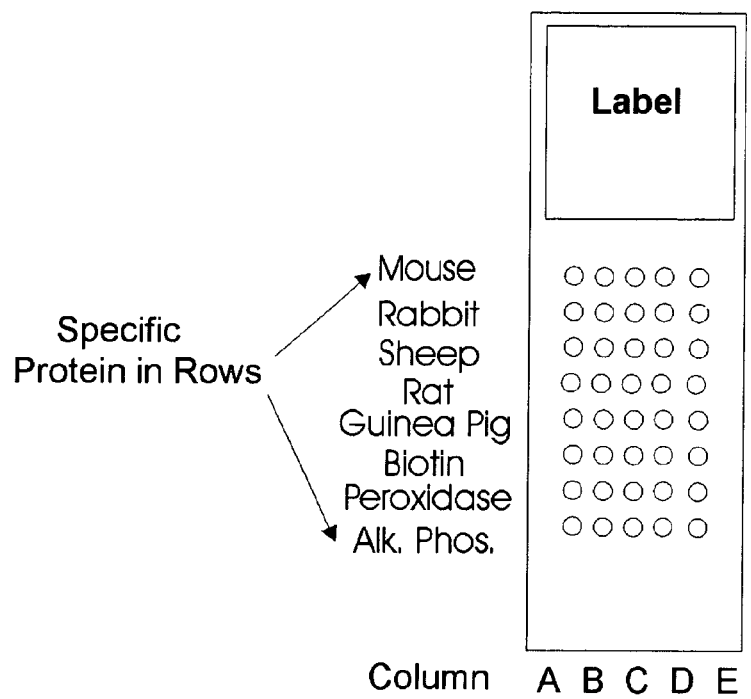
Column A: 100% specific protein
Column B: 50% specific protein
Column C: 25% specific protein
Column D: 12.5% specific protein
Column E: 6.25% specific protein
Diluent: Bovine Serum Albumin in PBS or Tris buffer, pH 6.7 to 7.0
*FIG_2*

QUALITY CONTROL OF ASSAYS

CROSS-REFERENCES TO RELATED APPLICATIONS

This application claims benefit of U.S. Provisional Patent Application No. 60/396,198 filed Jul. 15, 2002, the entire contents of which is incorporated herein by reference.

FIELD OF THE INVENTION

The present invention relates to a device for determining the quality of reagents used in an assay. The device contains reference quality control compounds which react with assay reagents to provide a measure of reagent quality, reagent stability, and assay performance. Methods for using the device in a variety of assay formats, particularly for immuno-based detection are described.

BACKGROUND OF THE INVENTION

Diagnostic assays are used in a variety of contexts for sample analysis. The assay may be for detecting the presence of specific analytes or used to assess the structural integrity or morphological changes in the sample being analyzed. For example, in the clinical laboratory, immuno-based assays are used to detect a myriad of analytes diagnostic of particular disease conditions. These assays may detect the presence of pathogenic organisms, such as viruses and bacteria; identify levels of a specified compound indicative of a disease condition; or reveal markers for cells and tissues involved in the disease process. In the area of analytical chemistry, analytical assays provide a rapid and simple method for detecting various organic and inorganic compounds, particularly for initial tests of a sample or as an adjunct to highly sensitive procedures such GC/mass spectroscopy and atomic absorption spectroscopy. For instance, the presence of antimony, barium, and lead found in firearm discharges are readily determined by reaction with sodium rhodizonate, which forms a colored product with the metals. Similarly, nitrates present as ammonium nitrate in explosives react with diphenylamine or diphenylamine derivatives to generate visible products.

In part, the sensitivity and the reproducibility of any such assays are affected by the quality of the assay reagents. Purity of ingredients used to prepare the reagents can vary. In addition, certain reagents degrade over time or are unstable under various physical conditions, such as temperature, pH, and light. Reagents also react with other reagents or the solvent, thus altering the reactivity and availability of the reagent. Since many standard clinical diagnostic assays are sold commercially in kit form, there will be batch-to-batch differences in the reagents because of manufacturing variations, even when commercial suppliers institute GMP (good manufacturing practices) standards.

Moreover, laboratory-to-laboratory performance of the assay can vary. This may arise from different operating procedures used in laboratories in terms of storage and handling of reagents. Additionally, the technician's skill, experience, and training can affect the quality of the assay result.

In order to generate consistency and accuracy in any diagnostic assay, it is beneficial to have some sort of quality assurance to validate the assay and the results obtained. This generates confidence in the data, and points out any problems that may arise in performing the assay. Validation of assay performance becomes critical with increasing complexity of diagnostic procedures, particularly where the assay involves a multitude of reagents and multiple process steps. For instance, an immunohistochemistry based diagnostic procedure practiced in a clinical laboratory may use an indirect conjugate or sandwich technique to determine the presence of a target analyte. Typically, this assay format involves exposure of hydrated slides containing a tissue sample to a primary antibody, which has no modifications to the antibody itself. This step is followed by exposure to a secondary antibody directed against the species in which the first antibody was raised. The secondary antibodies are typically composed of a mixture of antibodies (i.e., polyvalent), and may be obtained from a variety of animal species commonly used in the art to generate the primary antibody. Secondary antibodies have modifications that are capable of generating a visible staining reaction at sites where the primary antibody is bound to the specimen. To increase the detectable signal, secondary antibodies are commonly conjugated to small molecule ligands, such as biotin, capable of binding with high affinity to a cognate binding partner. After the secondary antibody step, the specimens are reacted with the high affinity binding partner, which typically has a label, such as an enzyme that acts on a suitable substrate (i.e., chromogen), to generate a visible, colored product in subsequent staining steps.

As described, this sandwich type immunostaining protocol has several points where amplification occurs: (1) at binding of the secondary antibody to the primary antibody, (2) at binding of the small molecule ligands to the high affinity molecule, and (3) at the enzyme action on the chromogenic substrate. The level of amplification at each of these points is difficult to evaluate because, typically, only the final signal, the presence of the colored product, is generally determined. Thus, it is difficult and time consuming to identify variations in reagent quality at each step of the assay and whether each step is working optimally. Moreover, due to the complex number of steps involved in the staining protocol, technical mistakes (e.g., omissions of steps) can be common, resulting in failures of the staining protocol.

Use of a known positive specimen does provide some level of control for assessing the staining procedure, but suffers from the problem that most methods of specimen fixation and processing affect the final signal obtained. Thus the actual stain intensity achieved on the control specimen compared to the unknown specimen cannot be compared in any quantitative fashion.

Thus it would be highly desirable to provide a way to verify that an assay protocol having multiple reagents and multiple process steps has been performed properly, as well as an assessment of the potential changes in reagent quality over time, and that an appropriate result was obtained.

SUMMARY OF THE INVENTION

In accordance with the objectives above, the present invention provides a device for determining the quality of reagents used in an assay. The device comprises a substrate to which is attached a plurality of control compounds, where each of the compounds is reactive with a different reagent used in the assay. A graded series of differing amounts of each control compound is attached to spatially defined sites on the substrate.

In one aspect, the substrate is a solid, non-porous substrate, preferably glass, plastic, quartz, silicon, or metal. Generally, the solid substrate has at least a first flat surface for the binding of the quality control compounds. Preferably, the substrate is an optically transparent substrate, particularly a glass substrate comprising a microscope slide.

The quality control compound comprises any suitable reference compound which reacts with the particular reagent and whose reaction is detectable. Consequently, the quality control compounds suitable for the present invention are determined by the assay and the reagents used. Various assays applicable to the present invention include chemical analytical assays; immuno-assays, particularly immunohistochemical assays; hybridization assays, particularly in situ hybridization and in situ amplification assays; histochemical stain assays; enzyme assays; and the like. Consequently, the quality control compounds comprise compounds which react with reagents used in these assays.

Because many assay reagents are directed to identifying presence of reactive functional groups on a compound, the quality control compounds comprise compounds containing these functional groups, including alkyls, alkanyl, alkenyl, alkynyl, aromatic rings, and aryl compounds. Functional groups include halo, hydroxyl, amines, imines, aldehyde, keto, carboxyl, amide, ester, nitro, nitrile, azo, azido, hydrazide, isocyanates, isothiocyanates, phosphorous, and sulfur groups. Included in the chemical classes are biological molecules, which include amino acids, proteins, nucleosides, nucleotides, nucleic acids, saccharides, oligo- and polysaccharides, lipids, sterols, and the like.

In another aspect, the quality control compounds comprise at least one ligand which reacts with a reagent comprising a binding partner of the ligand. Suitable combinations of ligand and binding partner include substantially complementary nucleotide base recognition molecules, substantially complementary homopolymeric nucleic acids or homopolymeric portions of polymeric nucleic acids; an epitope and an antibody which binds the epitope; biotin or iminobiotin and avidin or streptavidin; a ligand and its receptor; a carbohydrate and a lectin specific therefore; an enzyme and an inhibitor therefore; and an apoenzyme and cofactor. Exemplary ligand and binding partner combinations include chitin and chitin binding protein; mannose and mannose binding protein; transcription factor binding DNA sequences and cognate transcription factors; protein-protein interaction domains (e.g., phosphorylated SH2 domains); and cholesterol and cholesterol binding compounds digitonin, tomatine, filipin, and amphotericin B.

In another aspect, the ligand may comprise an epitope bound by a reagent antibody, where the epitope comprises a hapten, nucleoside, nucleotide, nucleic acids, saccharides, oligo- and polysaccharides, lipids, sterols, synthetic peptides, and proteins. In a preferred embodiment, where the assay reagent comprises non-primary antibodies, the quality control compound comprises serum proteins of the animal from which the non-primary antibodies are raised. Particularly preferred are serum proteins of mammals. In a particularly preferred embodiment, the serum proteins are selected from the group consisting of immunoglobulin isotypes IgG, IgM, IgA, and IgE.

In another aspect, the quality control compounds comprise enzymes detected by the assay, which include fluorescent, histochemical, chemiluminescent, and electrochemiluminescent assays. In particular, the enzymes comprise detection enzymes, which are indirect labels used to detect presence of a target analyte in a sample. The enzymes are attached to the substrate via chemical linker, peptide, protein, nucleic acid, or carbohydrates. Particularly preferred is a detection enzyme selected from the group consisting of β-galactosidase, horseradish peroxidase, alkaline phosphatase, glucose oxidase, β-glucouronidase, urease, glucose-6-phosphate dehydrogenase, and lactate dehydrogenase.

In addition to the quality control compounds, the device of the present invention may contain an identifying code, particularly a numerical or bar code. The code may represent information regarding the day and date, assay batch, type of quality control device, type of assay, laboratory performing the assay, identification numbers (PIN) for security and access, names or identifying codes of patients, personnel performing the assay, readouts and analysis of reaction of reference compounds and reagents, etc.

Another object of the present invention is to provide methods of using the described devices to determine the quality of reagents and to validate performance of the assay. In one aspect, the method comprises contacting a plurality of different reagents used in an assay with a substrate comprising a plurality of quality control compounds, where each quality control compound is reactive with at least one of the reagents. Different amounts of each control compound, particularly a graded dilution series, are bound to the substrate at a plurality of spatially defined sites. Following reaction of the reagent and quality control compound, the extent of the reaction is determined, generally by measuring or evaluating a detectable signal. The device may be used to determine the quality of both primary and secondary reagents. In a preferred embodiment, at least one secondary reagent is examined. In other embodiments, only the secondary reagents are examined. Assessing the extent of the reactions also provides an indication of assay performance.

In another aspect, the device is used to validate performance or determine reagent quality of at least one step of an assay. Specific steps of the assay rather than the whole assay are performed on the device. Steps involving both primary and secondary reagents may be tested. As above, steps involving at least one secondary reagent are examined. In other embodiments, steps involving only the secondary reagents may be examined.

In a further aspect, the device is used to compare the reagent quality and assay performance in one or more steps of a first assay and a second assay. The first assay may be performed by a first laboratory and the second assay performed by a second laboratory. Alternatively, the first assay is performed by a first technician and the second assay performed by a second technician. Comparison of the results provides a basis for determining performance of the laboratories or technicians, particularly for evaluating quality assurance of diagnostic laboratories.

In yet another aspect, the present invention is used in methods for assessing the quality of sets of reagents used to perform an assay. The method comprises performing the assay on a first device with a first set of reagents and performing the same assay on a second device with a second set of reagents. The first and second devices have the same quality control compounds attached to the substrate. Extent of reaction on the first and second devices is determined by measuring or evaluating a detectable signal. In one aspect, the first and second sets of assay reagents comprise different batches of reagents, thus allowing comparison of reagent quality in these different preparations. In another aspect, the first set of reagents comprise reagents stored for different time periods, either under different or the same storage conditions. Alternatively, the first set of reagents comprises reagents stored for defined time periods while the second set of reagents comprise a set of freshly prepared reagents. Shelf life of the reagents under various storage conditions is determined by comparing the reactions of the first and second sets of reagents.

In the present invention, determining the extent of reaction of reference compounds and reagents generally relies on a detectable signal. Detection basis includes radioactivity, absorbance, transmittance, light scattering, fluorescence, chemiluminescence, electrochemiluminescence, conductivity, etc. Particularly preferred are photometrically detectable signals. Particularly for immunohistochemical assays in which detectable signal involves generation of a colored, insoluble product, signal quantitation is by absorbance and/or light scattering. In one preferred embodiment, signal acquisition is carried out with a charge coupled (CCD) device or complementary metal oxide semiconductor (CMOS) device, and the signal quantitated, particularly by pixel counting.

The quality control devices of the present invention has other features and advantages which will be apparent from or are set forth in more detail in the accompanying drawings and the following Detailed Description of the Preferred Embodiments, which together serve to explain the principles of the present invention.

BRIEF DESCRIPTION OF THE DRAWINGS

FIG. 1 depicts the general format of the quality control device. The substrate is a glass slide with quality control compounds A-H. Each row contains on spatially defined sites a graded series of concentrations of an identified reference compound. In the illustrated embodiment, the concentrations range from undiluted (100%) to ten fold diluted (10%), with 10% difference in concentration between each defined site. Labels and identifying codes are printed onto the slide prior to attachment of reference compounds, and is done by screen or pad printing using catalyzed inks or paints, which are preferably resistant to the reagents used in the assay process. Optionally, the label also has a particular background color, which provides an additional basis for identifying the type of quality control slide. The bar code is a binary code readable by an automated assay processing machine to identify the type of slide, or other relevant information. Each row of reference compounds is additionally identified by number, alphabet, or code placed to the left end of each row.

FIG. 2 depicts a quality control device configured for immunohistochemical staining procedures. Serum proteins from mouse, rabbit, sheep, rat, and guinea pig are attached to a derivatized glass microscope slide at spatially defined sites. In addition, serum proteins conjugated to either biotin, horseradish peroxidase, or alkaline phosphatase are also placed onto the slide. Serum proteins containing the conjugated ligand or label are obtained from a different animal than the unconjugated serum proteins. Each reference compound is present in a graded dilution series of 100%, 50%, 25%, 12.5% and 6.25% (see Example 1).

DETAILED DESCRIPTION OF THE PREFERRED EMBODIMENTS

The present invention relates generally to a device for assessing the quality of reagents used in an assay, particularly an assay requiring a plurality of reagents and involving multiple processing steps. The device is adaptable for examining reagent stability, determining variations in different reagent preparations, and assessing the efficacy of the reagents used. In addition, the device provides a basis for determining the performance of each step of an assay and validating the assay data. The present invention allows evaluations of laboratory to laboratory performance and provides reliance on assay conducted on a particular sample. The device is especially applicable to clinical laboratories where multitude of samples is assayed.

The device of the present invention comprises a substrate which contains a series of dilutions of a specific quality control compound or reference compound that will give a positive reaction for each step of multiple step assay protocols. A plurality of quality control compounds are attached to the substrate in assessing the plurality of reagents used in an assay. By having quality control compounds for each assay step, the user will have a definitive indication that each step of the protocol has been performed in the correct sequence. In addition, by having multiple dilutions of each reference compound, the user will be able to assess the quality of the detection reagents used, as well as correct for any variation, should the results be analyzed in a quantitative manner.

Accordingly, the present invention relates to a device for determining the quality of a plurality of reagents used in an assay. As used herein, "reagent" comprises any substance used in detecting or measuring a component or target analyte, which may be chemical, inorganic or organic, or of biological constitution. Representative target analytes include, but are not limited to, drugs, antigens, haptens, antibodies, proteins, peptides, amino acids, hormones, receptors, enzymes, lectins, carbohydrates, lipids, steroids, cancer cell markers, tissue cells, viruses, bacteria, parasites, vitamins, nucleic acids, pesticides, environmental toxins, carcinogens, metals, and the like. The reagent is not limited to any particular chemical class or biological substance, and encompasses any type of reagents used in an assay, as described herein.

Reagents may be divided for description purposes into two general classes. "Primary reagents" are substances capable of reacting directly with the component or the target analyte to be assayed. Reaction is any specific physical and/or chemical interaction between the primary reagent and the component being detected or measured. Physical interaction may be non-covalent in nature, involving hydrogen bonding, hydrophobic effect, ionic interactions, and van der Waals forces, that are of sufficient specificity between the primary reagent and the component. An embodiment of this type of interaction is the binding of an antibody to a hapten or epitope against which the antibody was generated, or intercalation of ethidium bromide into a nucleic acid duplex.

Primary reagents may also react with the target analyte in a covalent manner resulting in a product distinct from the primary reagent and target analyte. In addition to covalent reactions, coordination complexes form another basis of molecular interactions, such as those found in organometallic compounds or metal-ligand chelates, for example ferrocene, magnesium-ethylenediaminetetraacetic acid (EDTA), or phenanthroline-copper complexes. As understood in the art, reactions may involve multiple types of reactions, covalent and non-covalent.

Another class of reagents is "secondary reagents" or "non-primary reagents" which encompass substances not within the scope of primary reagents. These include compounds that react with the primary reagents and are used to detect or measure presence of the primary reagent in the sample or after its reaction with the target analyte. In another aspect, the secondary reagents do not react with the primary reagent but are used in detection or measuring presence of the primary reagent. Secondary reagents may also comprise compounds used for purposes other than for detecting a specific target analyte. Embodiments of secondary reagent used in the context of an immunohistochemical assay include, by way of example and not limitation, a secondary antibody which binds to the primary antibody, a high affinity molecule which binds a small molecule ligand conjugated to the secondary antibody, an enzyme indirectly used for detecting or measuring presence of the target analyte, substrates for the enzyme, and additional chemical reactants used to detect the enzymatic product or enhance the signal produced by enzymatic activity. Histochemical stains used in an immunhistochemical assay as counterstains, or as stains to reveal various cellular and tissue structures, are considered herein as secondary reagents.

Generally, the present invention relates to determining the quality of both primary and secondary reagents. As discussed in further detail below, the quality control compounds are chosen to evaluate (1) the quality of reagents that interact directly with the component being analyzed (i.e., the target analyte), and/or (2) the quality of secondary reagents used to detect the presence of or interaction of the primary reagent or identify structures/compounds other than the target analyte. In one aspect, the present invention is directed to determining the quality of at least one secondary reagent used in the assay, and thus comprises at least one reference compound which reacts with one secondary reagent. In some embodiments, the present invention is directed to determining the quality of only the secondary reagents, in which case the device does not contain reference compounds that interact directly with the primary reagent, but contains only reference compounds which react with secondary reagents. Alternatively, in other embodiments, the present invention is directed to determining the quality of a plurality of only primary reagents, e.g., where multiple primary reagents are used in the assay.

In the present invention, the assay for which an assessment is done uses a plurality of reagents. A "plurality" or "multiple" or grammatical equivalents as used herein means more than one and at least two different types of reagents. As described in more detail below, the assays for which the present invention relates is not limited by the number of steps. It may comprise a process with a single step but using a plurality of reagents. Alternatively, the assay may comprise multiple steps, where any of the assay steps combined uses a plurality of reagents. Each step of such a multi-step assay process may use a single reagent or a plurality of reagents.

For evaluating the quality of reagents, the present invention comprises a plurality of control compounds. A "quality control compound", "reference compound", or "control compound" refers to a compound which reacts with at least one reagent. As discussed above, the term "react", "reaction" or "interaction" may be covalent or non-covalent in nature. In general, the quality control compound is used, directly or indirectly, to measure or detect the reagent. As will be appreciated by those skilled in the art, the types of reference compounds are not limited to any particular chemical class or biological material and is determined by the assay and the types of reagents in the assay. The skilled artisan following the guidance provided herein and with an understanding of an assay and its reagents can identify relevant, suitable control compounds for the present invention.

Generally, the plurality of reference compounds are selected such that each control compound is minimally reactive or non-reactive under assay conditions with reagents other than the reagent it is intended to react with. In other words, a reference compound reacts specifically under assay conditions with the intended reagent and minimally with other reagents. Minimally reactive refers to an acceptable level of crossreactivity which allows distinguishing the reaction of the reference compound with the reagent at issue from a reaction with another reagent used in the assay. Crossreactivity may be determined by reacting the reference compound with each reagent independently and comparing the results to reactions with combinations of the reagents. Acceptable levels of crossreactivity range from about 30% or less, preferably from about 20% or less, more preferably from about 5% or less, and particularly preferred from about 1% or less. However, greater than about 30% crossreactivity may be acceptable if the reactions with the different reagents are distinguishable.

In one aspect, the quality control compound comprises inorganic ions, particularly alkaline earth metals, transition metals, and certain post-transition metals, such as toxic heavy metals. In these embodiments, the reagent is a compound that reacts with the metal. Preferred alkaline earth metals include Ca and Mg. Preferred transition metals include Cr, Mn, Fe, Co, Ni, Cu, Zn, Ru, Rh, Pd, Ag, Au, Bi, Cd, Re, Os, and Hg. Preferred post transition metals include Pb.

The inorganic metal ions are attached to the substrate by known methods. In one aspect, gold is attached to substrates in the form of colloidal gold, or colloidal gold conjugated to other molecules, for example proteins (e.g., Hermanson, G. T., *Bioconjugate Techniques*, Ch. 14, Academic Press, San Diego, Calif. (1996); incorporated herein by reference). In another aspect, metals are bound to a substrate via chelating compounds attached to the substrate. Useful chelating ligands include, by way of example and not limitation, iminodiacetic acid; nitrilotriacetic acid (Porath, J. et al., *Nature*, 258:598 (1975); Hochuli, E. et al., *J. Chromatog.* 411:177 (1987)); diethylenetriaminepentaacetic acid derivatives; deferoxamine; and the like (Hermanson, G. T., et al., *Immobilized Affinity Ligand Techniques*, Academic Press, San Diego (1992); incorporated by reference). In a further aspect, the metals may be attached to the substrate via metal binding peptides or metal binding proteins, such as porphyrin containing proteins (e.g., hemoglobin, cytochrome C, etc.); $(His)_6$ Tag containing proteins; metallothionein; zinc finger and RING finger proteins; calmodulin and troponin C; and the like. These metal binding compounds may serve as useful reference compounds for any assay designed to detect presence of the described metal ions. Exemplary reagents include, by way of example and not limitation, anthraquinone dyes for calcium (e.g., alizarin red S and nuclear fast red); polymethine dye morin for detection of aluminum and calcium; dihydroxyazo dyes for calcium (e.g., eriochrome blue black B); monoazo dye bromo-PADAP for lead, copper, cadmium and other metals; dithiooxamide for copper; gloxal-bis(2-hydroxyanil) for calcium; triammonium salt of aurin tricarboxylic acid for aluminum(III); orcein, rhodanine, and rubeonic acid for copper (Bunton, T. E., *J. Comp. Pathol.* 102(1):25-31 (1990)); $(His)_6$ Tag proteins for the detection of nickel; and the like.

In addition, the reference compounds containing metal ions are useful for automnetallographic procedures in which metal particles are amplified to generate visible particulates (Stoltenberg, M. and Danscher, G., *Histochem. J.* 32:645-652 (2000); Danscher G., *Histochemistry* 81:331-335 (1984)). Automnetallography is a technique in which minute crystal lattices of gold or selenides and sulphides of silver, mercury, bismuth and zinc are enlarged by silver amplification to dimensions that can be visualized by light microscopy. This technique is particularly applicable for detecting presence of these metals in biological samples and in immunohistochemistry assays.

In another aspect, the quality control compound comprises a known compound containing a functional group reactive with a reagent used to detect presence of the reactive functional group. Reactive functional groups include, without limitation, halo, hydroxyl, amines, imines, aldehyde, keto, carboxyl, amide, ester, acyl halides, nitro, nitrile, azido, hydrazide, isocyanates. isothiocyanates, phosphorous, and sulfur groups. These and other chemical terms and structures described herein refer to definitions commonly understood and used by those skilled in the art. The known compound displaying the functional groups is of any chemical class, including, without limitation, alkyl, heteroalkyl, alkanyl, alkene, alkyne, aryl, and heteroaryl groups. Encompassed in the chemical classes are biological molecules, which include, by way of example and not limitation, amino acids, proteins, nucleosides, nucleotides, nucleic acids, saccharides, oligo- and polysaccharides, lipids, sterols, and the like.

By "alkyl" herein is meant a saturated or unsaturated, straight-chain, branched chain or cyclic monovalent hydrocarbon group derived by removal of one hydrogen atom from a single carbon of a parent alkane, alkene, or alkyne. The alkyl group may range from about 1 to about 30 carbon atoms ($C_1$-$C_{30}$), with a preferred embodiment utilizing about 1 to about 20 carbon atoms ($C_1$-$C_{20}$), with about 1 to about 12 carbon atoms ($C_1$-$C_{12}$) being preferred, with about 1 to about 5 carbon atoms ($C_1$-$C_5$) being especially preferred. In addition, encompassed within the definition of "alkyl" are cycloalkyl groups such as $C_5$ and $C_6$ rings, and heterocyclic rings with nitrogen, oxygen, sulfur or phosphorous. A substituted alkyl refers to an alkyl group further comprising one or more substitution moieties, defined as "R" groups. As used herein, "alkyl" is intended to encompass groups having any level of saturation, for example groups having single bonded carbon atoms, groups having one or more double bonded carbon atoms, groups having one or more triple bonded carbon atoms, and groups having mixtures of single, double and triple bonded carbon atoms. Compounds with specified level of saturation are referred to as alkanyl, alkenyl, and alkynyl.

Suitable R groups as used herein include, but are not limited to, hydrogen, alkyl, aromatic, amino, amido, nitro, nitrile, ethers, esters, aldehydes, carboxyl, sulfonyl, silicon moieties, halogen, sulfur containing moieties, phosphorous containing moieties, and ethylene glycols. It should be noted that some compounds contain two substitution groups, R and R', in which case the R and R' groups may be either the same or different.

By "alkanyl" herein is meant a saturated straight-chain, branched, or cyclic alkyl group. As described above, the alkanyl group may range from about 1 to about 30 carbon atoms ($C_1$-$C_{30}$), with a preferred embodiment utilizing about 1 to about 20 carbon atoms ($C_1$-$C_{20}$), with about 1 to about 12 carbon atoms ($C_1$-$C_{12}$) being preferred, with about 1 to about 5 carbon atoms ($C_1$-$C_5$) being especially preferred, and includes cyclic or heterocyclic rings.

By "alkenyl" herein is meant an unsaturated straight-chain, branched or cyclic alkyl group having at least one carbon-carbon double bond derived by removal of one hydrogen atom from a single carbon atom of the parent alkene. The alkene may be either of trans or cis configuration about the double bond.

By "alkynyl" herein is meant an unsaturated straight-chain, branched or cyclic alkyl having at least one carbon-carbon triple bond derived by removal of one hydrogen from a single carbon atom of the parent alkyne.

By "parent aromatic ring system" herein is meant an unsaturated cyclic or polycyclic ring system containing a conjugated π electron system. Encompassed within the definition of a "parent aromatic ring system" are fused ring systems where one or more of the rings are aromatic and one or more of the rings are saturated or unsaturated. Examples include, without limitation, benzene, anthracene, pyanthrene, triphenylene, trinapthalene, and the like. As used herein, "parent aromatic ring system" includes "heteroaromatic ring systems" in which one or more carbon atoms of a parent aromatic ring system are each independently replaced with the same or different heteroatoms, including, but not limited to N, P, O, S, B, Si, and the like.

By "aryl" group herein is meant an aromatic monocyclic or polycyclic hydrocarbon generally containing 5-14 carbon atoms, although it may include larger polycyclic ring structures. As used herein, "heteroaryl" or "heterocycle" refers to an aromatic group where one or more of the aromatic carbon atoms are replaced by the same or different heteroatoms, including but not limited to N, P, O, S, B, Si, and the like.

The following common definitions apply to other chemical groups: "alcohol" refers to —OH and alkyl alcohols —ROH; "amino" group refers to —$NH_2$, NHR, and NRR', with R being as defined herein; "amide" group refers to —RCONH— or RCONR' groups; carboxylic group refers to —COOH group, "esther" group refers to —COOR group; aldehyde refers to —CHO group; "nitro" refers to $NO_2$; "sulfur" groups refers to compounds containing sulfur atoms, including without limitation thia-, thio-, and sulfo-compounds, thiols (e.g., —SH and —SR) and sulfides (—RSR'—); and "phosphorous groups" refers to compounds containing phosphorous, including without limitation phosphines, phosphates, and phosphate-esters.

In another aspect, the control compounds of the present invention encompass classes of organic compounds comprising nucleosides, nucleotides, and nucleic acids. By "nucleosides" herein refers to a substituted or unsubstituted heterocyclic base covalently linked to the C1 carbon of a pentose sugar. Heterocyclic bases may comprise those found in nucleic acids, such as pyrimidines uracil, cytosine, or thymidine; and purines guanine and adenine. Other exemplary heterocyclic bases are purine analogs, including but not limited to, 2-aminopurine, $N^6$-methyl adenine, 7-methyl guanine, thioguanine, hypoxanthene, 7-deazaadenine, and 7-deazaguanine. Exemplary pyrimidine analogs include, but are not limited to, isocytosine, 4-thiothymine, 5-fluorouracil, and 5-bromouracil. Other classes of heterocylic bases comprise indoles and pyrroles. The pentose sugars of the nucleoside include pentoses substituted with an R, —OR, —NRR' or halogen groups, where each R is hydrogen or alkyl. Exemplary pentose sugars include without limitation ribose, 2-deoxyribose, dideoxyribose, 2'-aminoribose, arabinose, and the like. Nucleoside as used herein includes those with pentose sugar analogs, including without limitation, unsubstituted or substituted furanoses of more or less than 5 carbon atoms, for example erythroses and hexoses.

By "nucleotide" herein refers to a nucleoside in which the 2', 3' or 5' carbon is substituted with a phosphate ester. The number of phosphate ester groups include mono, di, and triphosphates, although more may be present. Include within the definition of nucleotides are nucleosides with phosphate ester analogs. Exemplary phosphate analogs include, but are not limited to, phosphodiesters, phosphotriesters, alkylphosphonates, phosphoramidites, phosphorothioates, phosphodithioates, phosphoramidates, and the like. In some cases, as further described below, nucleotide analogs include heterocyclic bases attached to alternative backbones.

By "nucleic acid" or "oligonucleotides" or "polynucleotide" or grammatical equivalents herein refers to at least two nucleotides covalently linked together. A nucleic acid will generally contain phosphodiester bonds, although in some cases nucleic acid analogs are included that may have alternate backbones comprising, for example, phosphoramide (Beaucage et al., *Tetrahedron* 49(10):1925 (1993) and references therein; Letsinger, *J. Org. Chem.* 35:3800 (1970); Sprinzl et al., *Eur. J. Biochem.* 81:579 (1977); letsinger et al., *Nucleic Acids Res.* 14:3487 (1986); Sawai et al., *Chem. Lett.* 805 (1984); Letsinger et al., *J. Am. Chem. Soc.* 110: 4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989)), O-methylphophoroamidite linkages (see Eckstein, F., *Oligonucleotides and Analogues: A Practical Approach*, Oxford University Press, UK (1991)), and peptide nucleic acid backbones and linkages (Egholm, *J. Am. Chem. Soc.* 114:1895 (1992); Meier et al., *Chem. Int. Ed. Engl.* 31:1008 (1992); Nielsen, *Nature,* 365:566 (1993); Carlsson et al., *Nature* 380:207 (1996), all of which are incorporated by reference). Other analog nucleic acids include those with positive backbones (Denpcy et al., *Proc. Natl. Acad. Sci. USA* 92:6097 (1995)); non-ionic backbones (U.S. Pat. Nos. 5,386,023; 5,637,684; 5,602,240; 5,216,141; and 4,469,863; Kiedrowshi et al., *Angew. Chem. Intl. Ed. English* 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580, "Carbohydrate Modifications in Antisense Research", Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994)); and non-ribose backbones, including those described in U.S. Pat. Nos. 5,235,033 and 5,034,506, and ASC Symposium Series 580, "Carbohydrate Modifications in Antisense Research", Y. S. Sanghui and P. Dan Cook Ed., Chapters 6 and 7. Nucleic acids containing one or more carbocyclic sugars are also included within the definition of nucleic acids (Jenkins et al., *Chem. Soc. Rev.* 169-176 (1995)). All of the cited references are hereby expressly incorporated by reference.

The nucleic acids may be single stranded or double stranded, or contain portions of both double stranded or single stranded sequence. The nucleic acid may be DNA, both genomic and cDNA, RNA or a hybrid, where the nucleic acid contains any combination of nucleotides, for example deoxyribo- and ribo-nucleotides, and any combination of bases, including uracil, adenine, thymine, cytosine, guanine, inosine, xanthine, hypoxathanine, isocytosine, isoguanine, etc (see, e.g., U.S. Pat. No. 5,681,702). It is to be understood that nucleic acid includes combinations of naturally occurring nucleic acids and nucleic acid analogs, for example oligonucleotides containing PNA and DNA (Lutz, M. J. et al., *Nucleosides Nucleotides* 18: 393-401 (1999) and Misra, H. S., *Biochemistry* 37: 1917-1925 (1998); publications hereby incorporated by reference).

In a further aspect, the "quality control compounds" or "reference compounds" comprise "amino acids" or "proteins". An "amino acid" as used herein refers to naturally occurring and synthetic amino acids. Naturally occurring amino acids may be categorized in various groups (Eisenberg et al., *J. Mol. Biol.* 179:125-142 (1984)), including, but not limited to, acidic amino acids, which generally have negatively charged side chains at physiological pH (i.e., glu and asp); basic amino acids, which generally have positively charged side chains at physiological pH (i.e., his, arg, and lys); polar amino acids, which have at least one bond where electrons are distributed unevenly towards one of the atoms (i.e., asn, gln, ser, thr, tyr); hydrophobic amino acids, which generally have the property of not forming energetically favorable interactions with water molecules (i.e., ile, phe, val, leu, tyr, met, ala, gly and tyr); aromatic amino acids, which have side chains having at least one unsubstituted or substituted aryl or heteroaryl groups (i.e., his, phe, tyr, trp); non-polar amino acids, which have a side chain not charged at physiological pH (i.e., ala, leu, pro, met, gly, val, iso, phe, try, and cys); aliphatic amino acids, which have an aliphatic hydrocarbon side chain (i.e., ala, val, leu, ile); and small amino acids, which have a side chain with three or fewer carbon or heteroatoms, and may be further classified as acidic, aliphatic, non-polar and polar amino acids (i.e., gly, als, val, ser, thr).

Other amino acids include amino acid analogs, either naturally occurring or synthetic. These include, but are not limited to, D enantiomers of the amino acids given above; ornithine, citrulline, norleucine, norvaline, homocysteine, homophenylalanine, phosphoserine, phosphothreonine, phosphotyrosine, hydroxyproline, and the like. All of the foregoing amino acids may be in L- or D-conformations. Chemical blocking groups or other chemical substituents may also be present (Green, T. W. and Wuts, P. G., *Protective Groups in Organic Synthesis,* 3rd Ed., John Wiley and Sons, New York, N.Y. (1999)).

By "protein" herein is meant at least two covalently attached amino acids and includes proteins, polypeptides, oligopeptides and peptides. The protein may be made up of naturally occurring amino acids or synthetic amino acid analogs, as discussed above. Generally, the covalent linkage is an amide or peptide linkage, although it is to be understood that the amino acids may be covalently attached by other than an amide or peptide linkage. Other types of linkages include substituted amide linkages and peptide mimetic linkages, also referred to as isosteres of peptide linkages. Peptide analogs having such linkages are well known in the art. The peptides and proteins may be linear or cyclic, and attached or complexed to other molecules, such as nucleosides, nucleotides, nucleic acids, saccharides (mono-, oligo- and polysaccharides), lipids, steroids, other proteins and peptides, aromatic compounds, and prosthetic groups, such as porphyrins and flavins.

Peptides and proteins useful as quality control compounds, include virtually any type of peptide or protein if reactive with at least one reagent in the assay. The peptide may react with the reagent by virtue of functional groups on the protein or by the particular sequence and structure, such as epitopes bound by antibodies, protein regions interacting with functional domains of other proteins, proteins which interact with nucleic acids, and proteins which interact with compounds containing saccharides. In another aspect, the proteins comprise enzymes acting on a reagent substrate, as further discussed below.

In a further aspect, the control quality or reference compounds comprise sugars or saccharides, and carbohydrates. Monosaccharides comprises the general formula $(CH_2O)_n$, where n ranges from 3 to about 8, and have two or more hydroxyl groups. Aldehyde containing monosaccharides are referred to as aldoses while keto containing monosaccharides are referred to as ketoses. Exemplary monosaccharides include, by way of example and not limitation, trioses glyceraldehyde and dihydroxyacetone; tetroses erythrose and threose; pentoses ribose, ribulose, and arabinose; hexoses glucose, fructose, and galactose; heptoses D-alloheptulose, L-glycerol-D-manno-heptose, and sedoheptulose; and octoses octulose and gluco-octose. One or more of the hydroxy groups of the monosaccharides can be replaced by either the same or different substituent R groups to form monosaccharide derivatives. Substitution R groups include, but are not limited to, hydrogen, amine, carboxyl, ethers, esther, amide, sulfur and phosphate containing groups, and the like. Exemplary modified monosaccharides include N-acetylglucosamine, glucosamine, and glucouronic acid.

By "oligosaccharide" or "polysaccharide" herein refers generally to compounds in which monosaccharide units are joined by a glycosidic linkage. Oligosaccharides include polymer chains having up to about 10 monosaccharide units. Exemplary oligosaccharides include without limitation disaccharides lactose, sucrose, fructose, maltose, and the like. Polysaccharide refers to long chain polymers of monosaccharides. Oligosaccharides and polysaccharides may be linear or branched, containing same or different monosaccharide units, without or with substituted hydroxyl groups. Exemplary polysaccharides include, by way of example and not limitation, cellulose, chitin, glycogen, starch, glycosaminoglycans, chondroitan sulfate, dermatan sulfate, keratan sulfate, and heparin. In certain forms, the monosaccharides, oligosaccharide, and polysaccharide may be attached to other molecules, particularly peptides and lipids, in the form of proteoglycans, peptidoglycans, glycosylated proteins, and glycolipids.

In yet a further aspect, the quality control compounds or reference compounds of the present invention comprise lipids. As used herein, lipids generally comprise water insoluble molecules soluble in organic solvents. In one aspect, lipids comprise a fatty acid, which comprises an aliphatic hydrocarbon chain with an acyl group, where the aliphatic chain is either a saturated or an unsaturated alkyl with one or more double bonds. Typical fatty acids include, without limitation, lauric acid, myristic acid, palmitic acid, stearic acid, oleic acid, linoleic acid, and linolenic acid. Fatty acids are or could be linked to acyl group carriers, such as glycerol, sphingosine, cholesterol, and others.

The lipids can also be classified into different lipid classes based on their polarity. Lipids may be nonpolar or polarlipids. Examples of such non-polar lipids are mono-, di- or triacylglycerols (glycerides), alkyl esters of fatty acids, and fatty alcohols. Polar lipids have polar head groups and exhibit surface activity, such as fatty amines, phosphatidic acid (e.g., phosphatidyl ethanolamine, phosphatidyl choline, etc.), phospholipids, glycolipids glycosylphosphatidylinositol), and the like. In certain forms, the lipids are attached or linked to nucleosides, nucleotides, nucleic acids, amino acid, proteins, or saccharides. Exemplary lipids attached to proteins include N-myristoyl, palmitoyl, and glycophosphatidyl inositol (see Thompson, G. A. and Okuyama, H., *Prog. Lipid Res.* 39, 19-39 (2000); Bauman, N. A. and Menon, A. K., *Lipid modification of proteins*. In: Biochemistry of lipids, lipoproteins and membranes, 4th Edition. pp. 37-54, D. E. Vance and J. Vance ed., Elsevier, Amsterdam (2002)).

In another aspect, the lipids comprise steroids, a tetracyclic compound based on hydrogenated 1,2 cyclopentenophenanthrene having substituents at the C-10, C-13 and C-17 carbon atoms. Typical steroids include, but are not limited to, cholic acid, desoxycholic acid, chenodesoxycholic acid, estrone, progesterone, testosterone, androsterone, norethindrone, cholesterol, digoxin, and the like. Steroid or sterols as described herein may be attached to or modified with nucleosides, nucleotides, nucleic acids, amino acids, proteins, saccharides, oligosaccharides, polysaccharides, and other lipids. Exemplary modifications include, by way of example and not limitation, cardiac glycosides in which a steroid molecule is attached to carbohydrates; digoxin attached to nucleosides/nucleotides; cholesterol attached to proteins (e.g., hedgehog protein; see Mann, R. K. and Beachy, P. A., *Biochim. Biophys. Acta*, 1529, 183-202 (2000)).

In a further aspect, lipids include isoprenoids comprised of isoprene units $C_5H_8$. Isoprenoids include various naturally occurring and synthetic terpenes, which may be either linear, or more typically cyclic, including bicylic, tricyclic and polycyclic. Exemplary isoprenoids include, by way of example and not limitation, geraniol, citronellal, menthol, zingiberene, β-santanol, β cadiene, matricarin, copaene, camphene, taxol, carotenoids, steroids, and the like. Isoprenoids may be attached to other molecules, including, but not limited to, nucleosides, nucleotides, nucleic acids, amino acids, proteins, saccharides, oligosaccharides, and polysaccharides. Prenylated proteins are formed by attachment of isoprenoid lipid units, farnesyl ($C_{15}$) or geranylgeranyl ($C_{20}$), via cysteine thio-ether bonds at or near the carboxyl terminus.

In the present invention, the reference or quality control compounds react with the reagents used in the assay. Thus, in one aspect, the quality control compound comprises at least one ligand, where at least one of the reagents is a binding partner of the ligand. The ligand and binding partner form a complex, preferably a complex of sufficient specificity to be stable under assay conditions. Typically, the binding constants are of about $10^6$ to about $10^{12}$, but may be higher or lower depending on multivalency and/or cooperativity of the interactions. The ligand and specific binding partner include, in either orientation, the following: (1) substantially complementary nucleotide base recognition molecules, substantially complementary homopolymeric nucleic acids or homopolymeric portions of polymeric nucleic acids; (2) biotin or iminobiotin and avidin or streptavidin; (3) a ligand and its receptor; (4) a sugar and a lectin specific therefore; (5) an antigen or hapten and an antibody or specific binding fragment thereof; (6) an enzyme and an inhibitor therefore; and (7) an apoenzyme and cofactor.

In one aspect, the ligand comprises a first nucleic acid and the binding partner comprises a second nucleic acid complementary to the first nucleic acid. If substantially complementary, the first and second nucleic acids form a stable hybrid. As used herein, nucleic acids are "complementary" or "substantially complementary" if the nucleic acids are sufficiently complementary to the target sequences to hybridize under normal assay (e.g., hybridization) conditions. Deviations from perfect complementary are permissible so long as deviations are not sufficient to completely preclude hybridization. However, if the number of alterations or mutations is sufficient such that no hybridization can occur under the least stringent of hybridization conditions, the sequence is not a complementary target sequence. In the hybridization reactions, the first and second nucleic acids may comprise synthetic oligonucleotides, cloned nucleic acid segments, genomic nucleic acids (either RNA or DNA), cDNA containing a known amount of a specific nucleic acid segment or sequence. As further described below, an RNA molecule may be converted to a DNA molecule for amplification or detection purposes by use of reverse transcriptase or other RNA directed DNA polymerases.

Typical hybridization reactions include in situ hydridization assays and also detection using nucleic acid arrays. For in situ hybridization, the sample, such as cells, tissue, or whole animals, is suitably fixed and then hybridized with a nucleic acid comprising a "detection probe," which is capable of hybridizing to substantially complementary nucleic acid sequences in the sample. As used herein, the nucleic acid segment or sequence being detected comprises a "target probe" or "capture probe." For use as a quality control compound, known amounts of target probe or capture probe are attached to a substrate and hybridized with the detection probe. The amount of detection probe hybridized is determined directly by the presence of a detectable label on the detection probe, or indirectly by a detectable signal from a binding partner which binds a label on the detection probe. Similar quality control compounds may be used to assess hybridization assays for nucleic acid arrays, where multiple target probes or the nucleic acids to be detected are attached to a substrate in an array format (e.g., Rampal, J. B., *DNA Arrays: Methods and Protocols*, Methods in Molecular Biology, Vol. 170, Humana Press, Totowa, N.J. (2001); Lashkari, D. A. et al., *Proc. Natl. Acad. Sci. USA* 94(24): 13057-62 (1997); hereby incorporated by reference).

The length of the nucleic acid capture probe can be of any sufficient length and sequence to produce a stable hybrid for detection. Capture probes may be whole chromosomes, particularly where the assay is by in situ hybridization of chromosomes (e.g., metaphase or interphase). In other embodiments, the capture probes are about 500 to about 5000 or more bases in length, particularly for hybridization to capture probes comprising genomic DNA, complementary DNA, or cloned nucleic acid segments. Alternatively, where large numbers of target nucleic acids are being detected, particularly in microarray formats, the capture probes are about 8 to about 500 bases, more preferably about 10 to about 100 bases in length. Methods of determining hybridization conditions and nucleic acid sequences suitable for detecting target probes are well known to the skilled artisan (e.g., Sambrook, J. et al., *Molecular Cloning: A Laboratory Manual*, Cold Spring Harbor Laboratory, Cold Spring Harbor, N.Y. (2001); Ausubel, F. M. et al., *Short Protocols in Molecular Biology*, 3rd Ed., John Wiley & Sons, NY (1995); publications hereby incorporated by reference).

In another aspect, the ligand comprises small chemical molecules bound by a binding partner used in an assay. An exemplary small molecule ligand is biotin or iminobiotin, which is bound by binding partners avidin, streptavidin, CaptAvidin biotin-binding protein, and NeutrAvidin biotin-binding protein (Molecular Probes, Eugene, Oreg.). Compounds conjugated to biotin include nucleotides, nucleic acids, proteins, and small organic molecules. Other ligand and binding partner combinations include, by way of example and not limitation, cholesterol and cholesterol binding compounds digitonin, tomatin, filipin, and amphotericin B; DNA binding protein binding sequences and cognate DNA binding proteins; protein-protein interaction domains (e.g., phosphorylated SH2 domains); polymerized actin and phallotoxins such as phalloidin, a bicyclic hexapeptide poison from the mushroom *Amanita phalloides*. Other ligand/binding partner combinations comprise ligand/receptor combinations, including peptide and steroid hormones and their corresponding receptors.

In a further aspect, the ligand comprises a saccharide and the binding partner comprises a compound which binds to the saccharide. A category of saccharide binding compounds include lectins, which are proteins or glycoproteins that bind or crosslink carbohydrates. For convenience of categorization, lectins may be defined according to related gene families. Galectins have specificity toward galactose and fall generally into three structural motifs—proto, chimera, and tandem repeats. C-type lectins comprise a family of calcium dependent carbohydrate binding proteins; an exemplary C-type lectin is collectins specific for mannose. Another C-type lectin, type II receptors, bind to carbohydrate ligands with multivalent interaction via oligomerization of the receptor. Selectins, for example L-selectin, E-selectin and P-selectin, bind to O-linked sugar chains and oligosaccharides with sialyl-Lex or sialyl-Lea groups. Annexins comprise a family of calcium- and phospholipid-binding proteins, with particular affinity for phosphatidylserine, phosphatidylethanolamine, and phosphatidylinositol. They are also known to bind glycosaminoglycans. Legume lectins have similar physicochemical properties between them but vary in their carbohydrate binding, and generally consist of two or four subunits, with each subunit having one carbohydrate-binding site; an exemplary legume lectin is ConA, which has variable saccharide specificity comparable to C-type lectins. Ricin is a family of lectin proteins having a heterodimeric structure, with a B chain which binds Gal/GalNAc and an A chain which is a RNA N-glycosidase. Tetrameric bark lectins (SNA and SSA) have sugar-binding specificity towards the Neu5Ac-alpha2-6Gal/GalNAc units. Other types of lectins include mannose binding lectins, such as MBP (mannan-binding protein), which binds to mannose or N-acetylglucosamine (GlcNAc) in a calcium-dependent manner; siglecs, a family of immunoglobulin (Ig) superfamily lectins that recognize glycans containing sialic acids; ttachylectins (e.g., tachylectins 1-5), comprising lectins which bind to agarose, dextran, 2-keto-3-deoxyoctonate of lipopolysaccharides (LPS), D-GlcNAc, D-GalNAc, staphylococcal lipoteichoic acids, S-type LPS from several Gram-negative bacteria having O-specific polysaccharides (O-antigens); and chitin binding protein which binds to chitin (Ooshima, T. et al., *J. Dent. Res.* 80:1672-1677 (2001)).

In another embodiment, the ligand comprises an epitope bound by an antibody used in the assay, particularly an immune-based assay. The ligand may comprise any compound bound by the antibody, particularly a compound against which the antibodies are made. In a preferred embodiment, the ligand bound by the antibody comprises a hapten. As used herein, "haptens" refer to small molecule compounds which are not by themselves sufficiently immunogenic and require carrier compounds to elicit an antibody response. Variety of chemical compounds serve as haptens, including, among others, alkyls, cyclic alkyls, aryls, heteroaryls, steroids, lipids, nucleosides, nucleotides, nucleic acids, and saccharides, particularly oligo- and polysaccharides, amino acids, particularly modified amino acids (e.g., phosphoamino acids), peptides, and the like. Small molecule chemical compounds acting as haptens, include, by way of example and not limitation, cocaine; nicotine; 2,4 dinitrophenol; digoxin; fluorescine, prostaglandins; bromo-uracil; and pyrethine.

In one aspect, the epitope is a region of a peptide or protein against which the antibodies are generated and to which the antibodies bind. The peptide or protein containing the epitope can be a naturally occurring protein, fragments thereof, or peptides or proteins generated synthetically. The protein may be part of an extract, such as a cell lysate, or in substantially purified form. Peptides include, among others, peptide hormones (e.g., neuropeptide Y, insulin, endorphins, etc.), cyclic peptide antibiotics, protein fragments, etc.

Because many immunological assays use a set of primary, secondary and sometimes tertiary antibodies to detect presence of a target analyte, serum proteins reactive with different antibodies may be used as reference compounds for such assays. Consequently, in a preferred embodiment, the serum proteins from different animals from which the primary, secondary, tertiary and other non-primary antibodies are obtained are attached onto the substrate. Serum proteins may be obtained from vertebrates capable of producing antibodies, generally birds (e.g., chickens, quail, etc.), and particularly mammals. As used herein, "serum proteins" comprise proteins remaining in the sera following removal of cellular bodies from blood, typically by coagulation. Thus, in general, sera substantially lacks firbrinogen and other clotting factors. Preferred are serum proteins from mammals, including but not limited to, artiodactyls (e.g., ungulates, etc.), carnivores (e.g., cats, canines, bears, etc.), cetacea, chiroptera (e.g., bats, etc.), lagomorphs (e.g., rabbits, etc.), perissodactyla (e.g., horse, donkey, etc.), primates, proboscidea, rodentia (e.g., mouse, rats, etc.), and metatheria (marsupials). Particularly preferred mammals include, among others, bovine, cat, chimpanzee, dog, donkey, goat, guinea pig, hamster, horse, human, mouse, monkey, rabbit, rat, sheep, and swine.

It is understood that serum fractionates into various proteins fractions: albumin, alpha globulin, beta globulin, and gamma globulins. Preferred are the serum fractions containing antibodies, generally the gamma globulin fractions. More preferably, the serum proteins comprise antibodies, particularly of immunoglobulin isotypes IgG, IgM, IgE, and IgA. Antibody class IgD is known to be present in trace amounts in the blood, and thus may have use in certain embodiments of the present invention.

As used herein, "serum" and "serum protein" does not refer exclusively to fluid formed by coagulation of blood of vertebrates. Invertebrates, such as arthropods and mollusks, contain a haemolymph, which bathes the cells and tissue and acts analogously to the blood found in vertebrates. The fluid plasma contains various nucleated cells, generally blood cells or haemocytes, involved in phagocytosis, encapsulation, wound healing, and coagulation. Numerous proteins are present in the haemolymph, including enzymes such as trehalase and other carbohydrates, hemocyanin-related proteins (e.g., hexamerins, etc.) involved in transport of hormones and other organic compounds and humoral immune defense; and biliverdin binding proteins (Tojo S. et al., *J. Insect Physiol*. 44(1):67-76 (1997)). Thus, serum of haemolymph may find uses in the present invention when such compounds are being analyzed, particularly by immuno-based approaches.

In yet another preferred embodiment, the quality control compound comprises an enzyme. The enzyme may comprise the compound being detected in the assay, such as enzymes localized in cells and tissue samples. Alternatively, the enzyme may be an enzyme used as an indirect label for detecting presence of a target analyte in the sample, such as when an enzyme is conjugated to an antibody for detection purposes. In one aspect, the reagent in such cases are substrates acted upon by the enzymes, the products of which are used as an indicator of enzyme activity. A variety of enzymes serves as markers in assays and can be categorized into the type of chemical reactions catalyzed: oxidoreductases, transferases, hydrolases, lyases, isomerases, and ligases.

Oxidoreductases are enzymes catalyzing oxidoreduction reactions and are described according to the groups upon which the enzyme acts. These groups include CH—OH, aldehyde or oxo, CH—CH, CH—$NH_2$, CH—NH, NADH OR NADPH, other N-containing groups, sulfur, heme, diphenols and related compounds, peroxide, hydrogen single donors+$O_2$, paired donors+$O_2$, superoxide radical, oxidizing metal ions, —$CH_2$, reduced ferredoxin, and reduced flavodoxin. Exemplary oxidoreductases, including, among others, catalase, thioreductase, peroxidases (e.g., myeloperoxidase, horseradish peroxidase, etc.), and superoxide dismutase.

Transferases comprise enzymes transferring a group from one compound (generally regarded as donor) to another compound (generally regarded as acceptor) and is described by the group or moiety transferred: one carbon, aldehydes or ketones, acyl, glycosyl, alkyl or aryl, N-containing, P-containing, S-containing and Se-containing groups. Exemplary transferases include, among others, glutathione S-transferase, choline acetyl transferase, protein kinases (e.g., serine-, threonine-, and tyrosine-kinases; phosphatidylinositol 3-kinase; etc.), terminal deoxynucleotide transferase, methyl transferases, glycosyl transferase, and transglutaminase.

Hydrolases comprise enzymes which catalyze the hydrolytic cleavage of specific bonds and is described by the cleaved bond: ester, glycosidic, ether, peptide, C—N (non-peptide), acid anhydride, C—C, C-halide, P—N, S—N, C—P, and S—S. Exemplary hydrolases include, among others, proteases (e.g., chymotrypsin, peptidase, chymase, tryptase, flavirin, calpain, etc.), glycosylases (e.g., β-galactosidase, α-galatosidase, uracil glycosylase, β-glucouronidase, etc.), phosphatases (e.g., baccterial alkaline phosphatase, acid phosphatase, calf intestine alkaline phosphatase, phosphoprotein phosphatase, apyrase, etc.), phospholipase, choline esterase, and nucleases (e.g., ribonuclease, DNase, exonuclease, endonuclease, etc.).

Lyases comprise enzymes which cleave C—C, C—O, C—N, C—S, C-halide, P—O, and other bonds by elimination, leaving double bonds or rings, or conversely adding groups to double bonds. These include, among others, decarboxylases, hydratases, chondroitan sulfate lyase, DNA glycosylase/apurinic lyase, argininosuccinate lyase, cysteine lyase, adenylate cyclase, guanylate cyclase, and phosphatidylinositol diacylglycerol-lyase.

Isomerases comprise enzymes which catalyze geometric or structural changes within one molecule without changing the chemical makeup, and are described according to the type of isomerism produced. These enzymes include racemases, epimerases, cis-trans isomerases, isomerases, tautomerases, mutases, or cycloisomerases. Exemplary isomerases include proline racemase, alpha-methylacyl-CoA racemase, N-acyl-D-glucosamine 2-epimerase, serine racemase, peptidyl-prolyl cis-trans isomerase (e.g., cyclophilin, FK506 binding proteins, etc), phosphogluco mutase, bisphosphoglycerate mutase, phosphoglycerate mutase, inositol-3-phosphate synthase, DNA topoisomerases I/II/III, and helicases (e,g.,DNA and RNA).

Ligases comprise enzymes catalyzing the joining together of two molecules coupled with the hydrolysis of a diphosphate bond in ATP or a similar triphosphate, and is described by the types of bonds formed: C—O, C—S, C—N, C—C, and P-ester. Exemplary ligases, include, among others, tRNA synthetases, anthranilate-CoA ligase, biotin-CoA ligase, ubiquitin ligases, folylpolyglutamate synthase, dihydrofolate synthase, pyruvate carboxylase, geranoyl-CoA carboxylase, DNA ligase (e.g., *E. coli*. and T4, etc.), RNA ligase, and RNA-3'-phosphate cyclase.

The enzyme classes described herein are not meant to be mutually exclusive since many enzymes have multiple functions and/or activities. For instance, certain hydrolases acting on ester, glycosyl, peptide, amide or other bonds catalyze not only hydrolytic removal of a particular group from their substrates, but also transfers the group to a suitable acceptor molecule. Additionally, hydrolytic enzymes might be classified as transferases, since hydrolysis itself can be regarded as transfer of a specific group to water as the acceptor.

Particularly preferred quality control compounds comprise enzymes used for signal detection as conjugates to an antibody or other binding partners, such as streptavidin. Widely used enzymes adaptable as indirect labels include, by way of example and not limitation, β-galactosidase, horseradish peroxidase, alkaline phosphatase, glucose oxidase, β-glucouronidase, urease, glucose-6-phosphate dehydrogenase, and lactate dehydrogenase.

In addition to enzymes and antibodies, diagnostic analysis relies heavily on chemical dyes and staining reagents that react with components in the sample. A "histochemical control compound" or "dye reference compound" refers to a known compound or composition which interacts with a chemical dye or staining reagent used in the assay. As will be appreciated by those skilled in the art, an appropriate histochemical control compound is determined by the dye or staining reagent. Dyes and staining agents have been classified according to various qualitative and chemical characteristics. For the present purposes, dyes and staining reagents will be described with regard to their chemical classes. Dye reagents include, but not limited to, general chemical classes of nitroso, nitro, azo, azoic, arylmethane; xanthene; acridine; phenanthridine; azole; oxazine; thiazine; polyene; polymethene; carbonyl; aza[18]annulene; and the like (*Conn's Biological Stains*, Horobin, R. W. and Kiernan, J. A. ed., 10th Ed., Biological Stain Commission, BIOS Scientific Publishers, Oxford, UK (2002); Haugland, R. P., *Handbook of Fluorescent Probes and Research Products*, 6th Ed., Molecular Probes, Eugene Oreg., (2002); both of which are hereby incorporated by reference). Many dye reagents react generally with nucleic acids, proteins, lipids, and saccharides through ionic, hydrogen bonding, hydrophobic, and van der Waals type of interactions. Some dyes interact through formation of covalent bonds and coordination complexes, such as periodic acid-Schiff stain for polysaccharides, Feulgen stain for DNA, alizarin red for bound $Ca^{2+}$, and dansyl chloride for detecting primary and secondary amino groups.

Exemplary compounds and corresponding quality control compounds include, by way of example and not limitation: monazo compound Janus Green B used to stain phosphoinositides; disazo compound ponceau S for staining proteins; diazonium salt Fast red TR for detecting esterase activity; diazonium salt Fast blue RR for detecting alkaline phosphatase, esterase, and β-glucouronidase activity; arylamethane compound Fast green FCF for staining and quantitating collagen and other proteins; arylmethane compound Coomasie brilliant blue R250 for staining proteins; arylmethane compound aldehyde fuchsine for staining cystein rich proteins and sulfated glycoproteins; hydroxytriphenylmethane Aurin tricarboxylic acid for the detection of aluminum; xanthene compound eosin Y for the staining of proteins; xanthene compound rhodamine B for the staining of keratin and lipids; xanthene compound pyronine Y for detecting the presence of RNA and DNA and staining of phospholipids; xanthene compound fluorescein isothiocyanate for reaction with nucleophilic groups, for example, amino, hydroxyl and thiol groups, particularly reactive groups on proteins and nucleic acids; acridine dye acriflavin for detecting sulfated glycosamininoglycans; acridine compound acridine orange for staining DNA and RNA and also starch granules; acridine compound phosphine for the staining of lipids and acid mucopolysaccharides; acridine compound quinacrine for the staining of nucleic acids; phenanthridine compound ethidium bromide for the detection of nucleic acids, particularly double stranded nucleic acids; azine compound nigrosine WS for the detection of proteins; azine compound neutral red for the detection of nucleic acids and lipid structures; azine compound safranine O for the detection of proteoglycans and glycosaminoglycans; oxazine compound nile red for the staining of lipids; oxazine compound gallocyanine chrome alum for the detection of DNA and RNA; oxazine compound nile blue for staining lipids and hydrophobic compounds, including DNA; oxazine compound nile blue for staining lipids and hydrophobic compounds, including DNA; thiazine compound azure B for detecting DNA, RNA, and mucin (i.e., highly glycosylated glycoproteins); thiazine compound toluidine blue for staining of sulfated mucins and amyloid proteins; polyene compound calcofluor white M2R for the staining of chitin and cellulose; polyene compound fluoro-gold for the detection of DNA and mucopolysaccharides; polymethine compound YO-PRO-1 for staining of DNA; polymethine compounds DiO, DiI, DiD for the staining of lipid membranes; benzimidazole compounds DAPI and Hoechst 33342 for the staining of nucleic acids; thiazole compound thiazole orange for staining nucleic acids; thiazole compound thioflavin T for staining amyloid proteins; flavinoid compounds hematoxylin and hematein, and derivatives thereof staining nucleic acids, phospholipids, starch, cellulose, and muscle proteins; carbonyl compound indoxyl ester and its derivatives for detecting esterase and glyosidase activities; anthraquinone compound alizarin red S for detecting calcium, particularly in calcified tissues; phthalocyanine compound luxol fast blue MBS for detecting myelin; phthalocyanine compounds cuprolinic blue to stain RNA and glycosaminoglycans, and alcian blue 8G for glycoseaminoglycans; osmium tetraoxide for the staining of lipids, including fats and cholesterols; iodine for the differential staining of starch, glycogen, and proteins; dithiooxamide and p-dimethylaminobenzylidenerhodamine for the assay of copper, for instance in detecting physiological abnormalities of copper metabolism; tetracycline and its derivatives for detecting the presence of calcium; and diaminobenzidine for detecting oxidases, such as peroxidase and catalase. This description is not meant to be exhaustive but illustrative of dye and staining reagents used in various assays and the compounds with which they interact.

It is to be understood that dyes and stains may be classified by other characteristics, including, acid dyes, azoic dyes, basic dyes, disperse dyes, mordant dyes, oxidation bases, reactive dyes, etc. In one aspect the histochemical stains comprise acid dyes, including, but not limited to acid fuchsine, aniline blue, eosin, and orange G. In another aspect, the histochemical stains comprise acid dyes, including, but not limited to, methyl green, methylene blue, pyronine, and toluidine blue. Other dyes useful for the present invention include Romanowsky-Giemsa stains, hematoxylin, hematein, and eosin. Compositions reactive with these dyes are described above and well known in the art.

As will be appreciated by those skilled in the art, the compounds and stains have applications for revealing structures in cells and tissues in addition to reactions with identified compounds. Binding of reagents to these cellular and tissue structures may occur through various components within the specimen (e.g., heterochromatic staining) rather than through a single cellular constituent. However, as will be appreciated by the skilled artisan, a specific compound known to react with the histochemical stain or dye may serve as quality control compound regardless of the cell or tissue being examined. Preferably, the quality control compound is similar to the components being detected in the cell or tissue structure, although different or combinations of control compounds may be used in some circumstances, particularly if informative of reaction of the histochemical stain.

In the present invention, the quality control compounds are bound to a substrate. The "substrate" comprises a material to which the compounds are bound and which is minimally reactive or nonreactive with the reagents used in the assay. Reactive substrates may be made minimally reactive or nonreactive by methods well known to the skilled artisan, as further described below. In one aspect, the substrates comprise matrix substrates, which refers to porous substrates, including filters or membranes, typically made of cellulose and cellulose derivatives (e.g., nitrocellulose, cellulose acetate, etc.); nylon; polytetrafluoroethylene (PTFE); polyvinylidene fluoride (PVDF); glass fiber; and the like. In another aspect, the matrix substrates are gel matrixes comprised of various polymer compounds, for example polyacrylamide, agarose, and dextran, which provide a three dimensional network of polymers for attaching quality control compounds (Proudnikov, D. et al., *Anal. Biochem.* 259:34-41 (1998); Guschin D, et al., *Anal. Biochem.* 250 (2):203-211 (1997); Arenkov P. et al., *Anal Biochem.* 278 (2):123-131 (2000); U.S. Pat. No. 5,858,653; all publications hereby incorporated by reference).

In a preferred embodiment, the substrate comprises a solid substrate. By "solid substrate" herein is meant a non-porous, non-matrix substrate. Various solid substrates, include, but are not limited to, those made of glass, plastic, quartz, silicon, and metals. Plastics useful in the present invention include, but not limited to, polypropylene, polystyrene, polyethylene, polyamide, polyethylenimine, polymethacrylate, PTFE, polyallylamine, and derivatives thereof (e.g., copolymer plastics). Metals include, but are not limited to, gold, silver, platinum, and metal oxides. As with other substrates, the solid substrate chosen is preferably nonreactive with any of the reagents used in the assay. More preferred are solid substrates having properties of optical transparency, especially when the assay uses an optical method for sample analysis. The substrates may also comprise combinations of solid substrates, such as glass and plastic, fused silica, silicon on glass, a first plastic and a second plastic, metal on silicon, etc. In some embodiments, the solid substrates are attached to "support structures" for providing support and rigid handling characteristics for the substrate. Generally, the support structures do not have quality control compounds bound directly on its surface, and may comprise, among others, glass, plastic, silicon, printed circuit board (PCB), and the like. The solid substrates can be laminated, attached, or deposited onto the surface of support structures, either as a uniform layer or as discrete, spatially defined sites.

Generally, the substrate comprises at least a first working surface to which the quality control compounds are bound. Preferably, the surface is flat and planar to allow uniform attachment and provide a consistent surface for exposure to reagent and subsequent analysis. Generally, the solid substrate may comprise a second surface parallel with the first surface and to which additional quality control compounds may or may not be attached. In a preferred embodiment, the solid substrate comprises a glass substrate comprising a microscope slide. Glass has excellent chemical resistance, is easily modified for attaching various compounds, and is optically transparent towards visible light. When an electrically conductive optically transparent substrate is necessary, conductive glass such as ITO glass or silicon may be used (Wang, C. H., *Analyst.* 127(11): 1507-11 (2002)).

The quality control compounds are bound, either covalently or non-covalently, to the substrate. Preferably the reference compounds are bound covalently to reduce loss or leaching of compounds from the substrate during the assay procedure, to provide proper orientation of molecules for efficiently interacting with reagents, and reduce non-specific adsorption of certain reagents to the surface. In one aspect, the compounds are bound directly to the substrate by depositing the compound on treated substrates capable of binding the compounds, or treating the deposited compounds under conditions that result in immobilization to the substrate. As is well known in the art, surface treatments include γ-irradiation, electron beams, plasma oxidation, and UV irradiation (Munro, H.S. *Polym Mater. Sci. Eng.* 58:344-348, (1988); Varga, J. M. et al., *FASEB J.* 4(9):2678-83 (1990); van Delden, C. J. et al., *Biomaterials.* 18(12):845-52. (1997); Bora, U. et al., *J. Immunol. Methods* 268(2):171-7 (2002)). For instance, surfaces of polypropylene, polystyrene, and polytetrafluoroethylene are activatable with radio frequency plasmas Ar and $NH_3$ to aminate the polymer surface (Mason, M., *Biomaterials* 21(1):31-6 (2000)). Treatments subsequent to deposition include, among others, UV irradiation, heating, and dessication.

In a preferred embodiment, the substrate surfaces are derivatized to add functional groups for subsequent attachment of the reference compounds. Numerous methods for derivatizing different types of materials are known in the art. Exemplary modification of glass and silicon surfaces include, but are not limited to, introduction of chlorine molecules via treatment with $SOCl_2$ and subsequent attachment of alcohol groups (Hergenrother, P. et al., *J. Am. Chem. Soc.* 122:7849 (2000)); derivatization with silane compounds, such as aminoarylsilanes, mercaptosilane, epoxysilanes (e.g., 3'glycidoxy propyltrimethoxysilane), maleimidesilanes, and aldehydic silanes (Guo. Z. et al., *Nucleic Acids Res.* 22:5456-5465 (1994); MacBeath, G. et al., *J. Am. Chem. Soc.* 121:7967 (1999); Shaltout, R. M. et al., *Mater. Res. Soc. Symp. Proc.* 576:15-20 (1999); derivatization with glyoxylyl compounds (Falsey, J. et al., *Bioconjugate Chem.* 12:346 (2001)); derivatization with isocyanate groups (Guo, Z. et al., *Nucleic Acids Res.* 22, 5456-5465 (1994)); and introduction of amino groups by coating with protein or polyamino acids, particularly poly-L-lysine or bovine serum albumin.

Methods for generating functionalized plastics are also well known in the art. Functionalized polystyrenes can be made by copolymerization with functionalized monomers or addition of functional groups to unfunctionalized polymers. Polystyrene substituents include bromine, nitrate, sulfonyl, carboxyl, aldehyde, and amino groups (Gonzalez-Vergara, E. et al., *J. Mol. Recognit.* 9:558-63 (1996); Keil, et al., *Biotech. Appl. Biochem.* 22:305-313 (1995)). Polyethylene may be partially oxidized to generate carboxyl groups (Luo, K. X. et al., *Proc. Natl Acad. Sci. USA* 92:11761-11765 (1995). PTFE substrates may be derivatized via an ammoniacal solution of sodium. Polypropylene, polyethylene and also glass can be modified via hydroxyl groups (Kumar, P. et al., *Bioconjug Chem.* 14(3):507-12 (2003)). These and other functional modifications of the described substrates are well within the skill of the art.

In some embodiments, particularly where the substrate comprises an electrode comprising a metal, the surface is modified to contain functional groups. Surface of gold substrates may be modified with alkane thiols, which react with the gold so that the alkane is covalently linked to the surface.

As needed, the functional groups on the substrates are sometimes modified to change the functional group for conjugation. Amines, aldehydes, ketones, carboxylates are readily modified with sulfhydral groups; amines react with various anhydrides, for instance succinic, glutaric, and maleic anhydrides to form carboxyl groups, while sulfhydral, imidazole, and thioether groups react with iodoacetate to form carboxyl groups; amines are introduced onto carboxyl groups by reaction with diamines; sulhydral groups may be converted to amine containing compounds by N-iodoethyltrifluoracetamide, ethyleneimine, or bomoethylamine; phenol structures can be modified to contain aromatic amines (e.g., aminophenyl); aldehyde groups can be introduced by oxidation of glycols, modification of amines with succimidyl aldehydes or glutaraldehydes; and the like (Hermanson, G. T., *Bioconjugate Techniques*, Academic Press, San Diego, (1996); hereby incorporated by reference in its entirety).

In another aspect, the functional groups are photoactivatable groups, which form covalent bonds with reactive groups present on the reference compounds. Typically, photoreaction is initiated with UV light, although other electromagnetic radiation may be used depending on the photoactivatable group. Photoactivatable groups may comprise aryl azides and halogenated aryl azides, such a phenylazide; benzophenone derivatives; diazo compounds, such as diazopyruvate; and diazirine compounds such as 3-triflurom-ethyl-3-pghenyl diazirine. As further discussed below, these may be attached to the substrate via crosslinking agents containing the photoactivatable group and a second reactive group.

Activation of functional groups and coupling of the quality control reagents to the substrates are done by methods well known in the art, particularly through the use of activating reagents and linking moieties, such as homobifunctional and heterobifunctional crosslinking agents, and trifunctional crosslinking agents (Pierce Applications Handbook/Catalog, Pierce Biotechnology, Rockford, Ill. (2002); incorporated by reference) Activating agents for coupling purposes include, but are not limited to, carbodiimide, 1-ethyl-3-(3-dimethylaminopropyl)carbodiimide, dicyclohexyl carbodiimide, N,N-ethyl-3-phenylisoxazolium-3-sulfonate, carbonylimidzole, anhydrides, and the like.

Homobifunctional crosslinkers having a spacer connecting same reactive functional groups include, but are not limited to, N-hydroxysuccimide esters such as dithiobis (succimidylpropionate), disuccimidyl suberate, disuccimidyl tartarate, etc.; imidoesters such as dimethyl adipimidate, dimethyl pimelimidate, dimethyl suberimidate, etc.; formaldehyde and bis-aldehydes such as glutaraldehyde; bis expoxides such as 1,4-butanediol diglycidyl ether; hydrazides such as adipic acid dihyrazide and carbodyhydrazide; bis-diazonium compounds bis-diazotized o-tolidine and bis-diazotized benzidine; and sulfhydral reactive reagents 1,4-Di-[3'-(2'-pyridyldithio)propionamido]butane, bis maleimides, difluorodinitrobenzene.

Heterobifunctional crosslinkers have various combinations of two different reactive functional groups linked by a spacer. These include, but are not limited to, combinations of amine and sulfhydral reactive groups, carbonyl and sulfhydral reactive groups; and photoreactive groups attached to amine, sulfhydral, carbonyl and carboxylate reactive groups. Exemplary heterobifunctional crosslinkers include, by way of example and not limitation, N-succimidyl 3-(2-pyridyldithio)propionate; succimidyl-4-(N-maleimidomethyl) cyclohexane-1-carboxylate; maleimidobenzolyl-N-hydroxysuccimide ester; succimidyl 6-(iodoacetyl) amino) hexanoate; 4-(4-N-maleimideophenyl)butyric acid hydrazide; N-hydroxysuccimidyl-4-azidobenzoate; p-nitrophenyl diazopyruvate; benzophenone-4-iodoacetamide; p-azidobenzoyl hydrazide; N-[4-(azidobenzoyl)oxy]succinimide; and the like.

In some embodiments, the quality control compounds are attached or tethered to the substrate through the use of "spacers." The spacer extends the attached reference compound away from the surface, thereby reducing steric hindrance of the substrate and enhancing access of reagents to the attached compounds. The spacers may comprise part of the crosslinking agent as discussed above, or is separately attached to the substrate, whereby the reactive group is presented away from the substrate surface. The linker can be hydrophilic or hydrophobic, semi-rigid or flexible, and optionally substituted with one or more substituents, which may be reactive functional groups to provide additional points for conjugation. In certain embodiments, the spacer is attached to the reference compound and contains a functional group capable of reacting with the substrate. Various linkers are known in the art, and comprise alkyls, alkenes, alkynes, aryls, heteroaryls, and the like. The linkers may include functional groups such as amines, imides, aldehydes, carbonyls, ethers, thioethers, carboxamides, etc.

In one aspect, the preferred linkers are from 1 to about 20 atom long, more preferably about 1 to about 10 atom long alkyls or heteroalkyls, where the atom or heteroatom is selected from the group consisting of C, N, 0, and S. The linker may also comprise a polypeptide, oligosaccharide, polysaccharide, or a saturated or unsaturated, substituted or unsubstituted alkanyl, alkene, alkyne, aryl or heteroaryl compound. Hydrophilic linkers may comprise polyethers such as polyalkyleneglycols, for example polyethyleneglycol or other polyalcohols.

The choice of a particular linker moiety is well within the capabilities of those skilled in the art. For instance, photoreaction with azidoaniline in the presence of 1,3-diaminopropane (DAP) is useful for attaching carbohydrates to polystyrene. In another carboxyl groups are introduced into polystyrene substrates by permanganate oxidation in sulfuric acid and subsequent activation with water-soluble carbodiimide and grafting with N-methyl-1,3-propane diamine to introduce a free secondary amino group on the support (Zammatteo N, *Anal. Biochem.* 236(1):85-94 (1996)).

In the present invention, the quality control compounds are attached on spatially defined sites of the substrate. In some embodiments, a single defined site is used for each reference compound, particularly when only an indication is needed to affirm that a step in the assay was performed. This format is useful where only a positive/negative control is desirable. In a preferred embodiment, the quality control compounds are attached on a plurality of spatially defined sites of the substrate. By 'plurality' herein is meant more than one and at least two sites. Generally, the number of sites needed is a range in the amount of control reactive compound which will provide a sufficient signal indicative of the concentration of reagent. Typically, each defined site contains a different amount of the quality control compound to provide a range capable of producing a linear response to the reagent concentration. In a preferred embodiment, a serial dilution series is made and the compound attached onto the substrate, where the dilutions encompass the requisite range of quality control compound needed to give a determination of the quality of the reagents, validate performance of the assay, and establish the reagent stability or shelf life. Determining the concentration range required and the number of spatially defined sites needed are well within the skill of those in the art.

Generally, each set of a reagent compound may be placed in an ordered array on the substrate. Spatially defined sites containing the quality control compounds may be separated from each other, or juxtaposed side by side. The shape of the spatially defined sites may be any geometric form, preferably circular, square or rectangular, which permit quantitation of the resulting detectable signal. In a preferred embodiment, the different quality control compounds are placed in separate parallel arrays. In addition, duplicates, triplicates, or more replicas of quality control reagent dilution series are used to measure accuracy and precision of the device, and in assessing assay performance and validation.

Optionally, the sample to be assayed may be placed onto the substrate of the present invention for simultaneous processing of sample and reference compounds. As will be appreciated by those in the art, the sample may comprise any number of materials, including, but not limited to, bodily fluids (including, but not limited to, blood, urine, serum, lymph, saliva, anal and vaginal secretions, perspiration, semen etc.), hair, cells, tissues, and cell lysates of virtually any organism, with mammalian samples being preferred, and human samples being particularly preferred. Other samples include environmental samples, including, but not limited to, air, agricultural, water and soil samples; biological warfare agent samples; research samples (e.g., in the case of nucleic acids, the sample may be the products of an amplification reaction, such as PCR amplification reaction); purified samples, such as purified genomic DNA, RNA, proteins, etc.; raw samples (e.g., bacteria, virus, genomic DNA, etc.). As will be appreciated by those in the art, any manipulation may have been done on the sample.

In addition to the various reference compounds, the device has an identifying code placed onto the substrate or support structure. Codes or identifiers can be placed directly onto the surface, or embedded or attached to the device by use of an adhesive unaffected by the assay process. The code may comprise a bar code or a numerical code. In other preferred embodiments, an optical code will be used to encode the information. An "optical code" herein refers to color combinations corresponding to a particular type of information, as further detailed below. The optical code may be various combinations of visible colors, various fluorescence compounds with differing excitation and emission spectras, and the like. In another aspect, the identifying code is an optical memory system in which data is stored on a heat-sensitive material via a computer controlled laser beam which either melts the sensitive material or changes its color, such as those memory systems found on compact optical discs. An optical device reads the patterns or digital codes.

In yet another embodiment, the identifying code comprises an electronic code. These may be placed on magnetic particles, magnetic tape, or magnetic strips placed on or into the substrate or support structures. Alternatively, microchips may be placed on the surface or embedded in the device for information storage and retrieval. Similar to "smart cards," the device may contain an integrated circuit (IC) microprocessor which can process and store data on a chip (microprocessor systems). In another embodiment, the microchip is an integrated circuit (IC) memory chip which can store data, but has no processor with which to manipulate that data (memory systems). Memory systems are dependent on a reader and also for their processing, and are suited to uses where the card performs a fixed operation. Types of information storage and retrieval systems include contact systems that require physical touch between the terminal reader and the surface of the device and contactless systems which interact with the reader using an electromagnetic coupling. Contactless systems are also referred to as "proximity" systems. In certain embodiments, dual mode systems incorporating contact and contactless interfaces are used in the device (Rankl, W. and Effing, W., *Smart Card Handbook*, 2nd Ed., John Wiley & Sons, New York, N.Y. (2000); hereby incorporated by reference).

Information stored on the device include, among others, day and date, assay batch, type of quality control device, type of assay, laboratory performing the assay, PIN identification numbers for security and access, names or identifying codes of patients, personnel performing the assay, readouts and analysis of reaction of reference compounds and reagents, etc. Thus, any type of relevant information may be stored and retrieved from the devices of the present invention.

The device of the present invention is prepared by standard techniques known in the art. As discussed above, substrate surfaces may be derivatized to attach quality control compounds, particularly for covalent attachment. Substrates lacking functional groups are treated to introduce functional groups, which allows the substrate to be further modified or activated as described. Optionally, spacers, if desired, are attached to the functionalized surface. The derivatization is carried out for all or substantial part of the substrate surface. Alternatively, spatially defined sites are modified. If irradiation is used, derivatization of the surface at discrete sites is accomplished by use of focused light, for example by use of UV lasers, or by the use of photomasks, which allow illumination of specific sites on the substrate. When chemicals are used, these may be applied to defined areas by methods detailed below.

The quality control compounds having reactive functional groups are spotted, deposited, or layered onto the substrate. Layering is done by immersion of the device in a solution of the compound, by spraying the compound onto the substrate, or by evaporating the compound onto the substrate surface. In a more preferred embodiment, the quality control compounds are attached to spatially defined sites on the substrate. A variety of methods are available in this regard. In one aspect, the quality control compounds are spotted onto the surface, either by a pipette or by use of a stylus, such as a pin (e.g., quill pin or split pin printer, etc.) or a stamping block for contact printing (see, e.g., Shalon, D. et al., *Genome Res.* 6:639-645 (1996); GMS 417 Arrayer, Affymetrix, Santa Clara, Calif.). When stylus or pins are used, adapting robotic systems allow for precise spatial positioning of the stylus on the substrate and rapid preparation of multiple copies of the devices (e.g., Biomek 2000, Beckman, Fullerton, Calif.; GMS 417 Arrayer, Affymetrix, Santa Clara, Calif.).

In another aspect, application of reference compounds is carried out using an ink jet system. Multichannel ink jet print heads allow deposition of different solutions simultaneously, although single channel systems may be used. Typically, a piezoelectric block is used to form the printhead, and channels in the printhead allow passage of fluid into an orifice used to deposit the compounds. Either the printhead or the substrate moves in defined steps along an XY axis while voltage pulses to the piezoelectric printhead control delivery of the reference compound (Lipshutz, R. J. et al., *Nat. Genet. Microarray Suppl.* 21:20-24 (1999)). A microprocessor system controls the printing system and allows the user to control the deposition pattern, dispensing time, and voltage to the printhead. An indicator compound, which does not react with the reagents or the quality control compounds, is optionally added to the solution to provide an assessment of printing quality. Useful indicator compounds include, among others, fluorescent molecules, for example rhodamine, or visible stains.

In another aspect, the printing system is a bubble jet system. Generally, in a bubble jet system, a small volume of reference compound solution is superheated to form a vapor bubble, which expands to create pressure on the surrounding fluid present in a chamber. The pressure from the expanding vapor forces a droplet of solution to eject from an orifice, thus resulting in deposition on a substrate. Because a bubble jet print head heats the solution, this system is used for reference compounds generally insensitive to temperatures, for example nuclei acids and small organic compounds.

In another aspect, the compounds are deposited by electrospray (Avseenko, N. V., *Anal Chem*. 74(5):927-933 (2002); Morozov, V. N. et al., *Anal Chem*. 71(15):3110-3117 (1999)). Generally, electrospray deposition involves producing liquid aerosols through electrostatic charging. Liquid droplets passing through a fine nozzle are electrically charged to a high voltage. As the liquid becomes highly charged, it reaches a critical point at which it disperses into a cloud of tiny, highly charged droplets. The result is deposition of smooth even films. Electrospray methods are adaptable to virtually all compounds, including, but not limited to, small organic molecules; amino acids and peptides; saccharides, including oligo- and polysaccharides; nucleosides, nucleotides and nucleic acids; and the like.

As will be appreciated by those in the art, subsequent to deposition of the reference compounds, the device is subjected to conditions that foster attachment of the compounds to the substrate. For non-covalent attachments, the device is treated to physical factors, for instance, heat or dessication. When the attachment is covalent, the device is incubated under conditions that foster covalent bond formation. These conditions will depend on the reactive functional groups on the substrate and the reference compound. Selecting suitable conditions is well within the skill of those in the art. For instance, carbonyl groups such as aldehydes, ketones and glyoxals react with amines to form labile Schiff base intermediates which can revert back to the starting compounds. This labile Schiff base may be stabilized by reduction, typically with sodium borohydride or cyanoborohydride. When the reactive functional groups are photoreactive groups, the substrate with deposited reference compounds is exposed to the appropriate wavelength light, for example UV irradiation for aryl azides and certain photoreactive diazo compounds. Use of directed light and/or a photomask provides control over linkage of the compounds to defined sites on the substrate (see, e.g., Fodor, S. P. et al., *Science* 251(4995):767-73 (1991); Nuwaysir, E. F. et al., *Genome Res*. 12(11):1749-55 (2002); hereby incorporated by reference). It is to be noted that certain biological compounds, such as proteins and nucleic acids are capable of forming covalent bonds when illuminated with UV light, and thus provides an additional basis for covalently attaching the compounds to the substrate.

Subsequent to attachment of the reference compounds to the substrate, any remaining reactive functional sites are blocked. This blocking procedure prevents further conjugation or modification of the substrate and reference compound, and also limits any undesirable reactions with the reagents. Preferably, the blocking agent is inert with the reagents and other compounds used in the assay. Typically, the blocking agent comprises a small organic molecule, although depending on the functional group and the reagents, molecules such as peptides, saccharides, and nucleic acids may be used. Selection of a suitable blocking agent is well within the skill of the art, and will take into account the reactive functional groups and the chemical nature of the reagents. Modification to another functional group is possible if the resulting group is not reactive with the reagents in the assay. Amine groups may be blocked with N-hydroxxysuccinimide acetate and anhydrides, such as acetic and maleic anhydride. Sulfhydral groups may be blocked with N-ethylmaleimide, iodoacetate, or dipyridyl sulfide. Aldehydes may be blocked with ethanolamine or other small amine containing compounds (e.g., glycine) followed by reduction. Carboxyl groups may be blocked by reaction with ethanolamine in the presence of carbodimides. Isothiocyanate groups may be blocked with small amine containing compounds such as amino acid glycine. Agents for blocking surfaces, particularly to block nonspecific interactions, also include, without limitation, inert proteins (e.g., BSA, gelatin, etc.) and hydrophilic polymers (e.g., polyvinlypyrrolidine and polyvinylalcohol, etc.).

Once made, the device is used in a variety of ways to determine the quality of reagents used in an assay. Generally, the device is processed using the same reagents and steps used to perform the assay on a sample. This may be done contemporaneous with or separately from processing of a particular sample. By performing the assay simultaneously on the device and the samples, a direct evaluation of assay performance and reagent quality is possible. The results of the assay on the sample are readily validated by the readouts from the present invention, thus providing quality assurance in assay performance.

Generally, the quality of reagents is determined by contacting a plurality of different reagents with the device comprising the plurality of quality control compounds. Each quality control compound present on a plurality of spatially defined sites is reactive with at least one reagent used in the assay. In a preferred embodiment, different amounts of control compound are present on each discrete site, and thus reacts to a different extent with the reagent. After processing of the device through all steps of the assay or a particular step, the reaction of the quality control compound and the reagent on each spatially defined site is assessed, as further described below. Omitting a reagent provides a negative control for assessing the reaction and provides information on any cross-reaction of reagents with the various reference compounds.

In one aspect the device is used to assess the performance of at least one step of the assay. The device is processed through specific steps of the assay, rather than all of the assay steps, and then reaction of the quality control compounds assessed. In this use of the device, an evaluation is made of reagents and performance of at least one or more steps of the assay. In one embodiment, steps involving only secondary reagents may be examined. In other embodiments steps and reagents using both primary and secondary reagents are assessed.

In a further aspect, the device is used to compare the performance of an assay and reagent quality in at least one or more steps of a first assay and a second assay. If the first assay is performed in first laboratory or by a first technician, and the second assay performed by a second laboratory or by a second technician, quality of laboratory or technician performance is readily determined by comparing the results of the first and second assays. These types of comparisons provide methods for quality assurance testing of diagnostic laboratories, and evaluation of the technical ability of laboratory staff. Such testing encourages proper implementation of standard diagnostic and analytical assays.

In a further aspect, the present invention is used in methods of assessing the quality of different batches of reagents or reagent shelf life. The method comprises performing an assay on a first device with a first set of assay reagents. The same assay is performed on a second device having identical quality control compounds using a second set of assay reagents. The reactions of the reagents with the quality control compounds on the first and second devices are detected and the resulting signal compared. The first set of assay reagents comprises a set of control reagents against which the second set of assay reagents comprising test reagents are compared. It is to be understood that the method of assessing reagent quality is not limited to a first set of assay reagents and a second set of assay reagents. Other sets of assay reagents may be tested as well. In one aspect, the first set of assay reagents comprise reagents made as different batches, either at different times, at the same time, or by different manufacturers. Thus, performing the assay on the quality control devices and comparing the readouts is an effective way of comparing the quality of different preparations of reagents.

For determining reagent shelf life, a first set of assay reagents comprise reagents made at a first time point, and a second set of assay reagents comprise the same reagents stored for a defined period of time. Storing a set of assay reagents for a defined time period and preparing a fresh set of assay reagents for comparison purposes may also achieve this effect. In the latter case, the fresh set of reagents is used as the control reagents while the stored set of reagents comprises the test reagents. Performing the same assay on the devices of the present invention with the different sets of reagents and comparing the readouts of the reactions provide a measure of any deterioration or changes in quality of the test reagent in the defined time period. Determining the reagent quality over a number of different time periods gives an indication of reagent shelf life.

The present invention is applicable to a variety of different assay formats. Generally, the assays comprise methods for detecting target analytes that include, among others, inorganic molecules; small organic molecules; amino acids and proteins; saccharides, including oligo- and polysaccharides; nucleosides, nucleotides, and nucleic acids; lipids; steroids; derivatives and combinations thereof. In another aspect, the assays comprise methods of assessing structures or morphology in a sample, particularly cell and tissue samples. As those skilled in the art will appreciate, evaluating structures or morphology and detecting target molecules are not exclusive, and overlap extensively in diagnostic assays.

In one aspect, the present invention is used in immune-based assays. As used herein, "immune-based" assays comprise methods of detecting target analytes or identifying structures using antibodies as a reagent. Antibodies include polyclonal, monoclonal, Fab fragments, recombinant antibodies, humanized antibodies, etc. As discussed above, the antibody reagents may comprise primary reagents and/or secondary reagents. As such, the primary antibody reagents react directly with the target analyte while secondary antibody reagents are used in an indirect manner to detect the analyte or structure. In certain embodiments, the antibodies bind to a target analyte and prevent its interaction with molecules or structures in the sample. Thus, any assays using antibodies, many of which are known in the art, are included within immune-based reactions.

In a preferred embodiment, the immune-based assay comprises an immunohistochemical assay, numerous formats of which are known in the art. Generally, samples to be examined are affixed to a substrate, either covalently or non-covalently, and the assay performed on the affixed sample. Variations on immunohistochemical assays, include, by way of example and not limitation, direct conjugate labeled antibody methods; indirect or sandwich methods; unlabeled antibody methods, such as the enzyme-bridge method; enzyme anti-enzyme methods (e.g., peroxidase anti-peroxidase, etc.); biotin-avidin/streptavidin systems; polyvalent methods; and enzyme-labeled antigen procedures (Taylor, R. T. and Cote, R. J. *Immunomicroscopy: A Diagnostic Tool for Surgical Pathologists*, 2nd Ed., W B Saunders, Philadelphia, Pa., (1994); hereby incorporated by reference). As is known in the art, various combinations of immunhistochemical techniques and procedures may be used. For instance, an indirect or sandwich method may use a primary antibody, a secondary antibody directed against the primary, and an avidin-bitoin/strepavidin system for detection.

As provided in detail above, the particular reagents used in the assay determines the quality control reagents to be used in the device of the present invention. By way of example for an immunohistochemical assay, the indirect sandwich procedure described above comprises a primary antibody, which binds to a target analyte in the sample, and a secondary antibody directed against the primary antibody. The secondary antibody is generally made against the antibody—in particular, the antibody of the same isotype—of the animal from which the primary antibody was generated. The secondary antibody is conjugated to a ligand, biotin, which is detected using its cognate binding partner, avidin or streptavidin. By conjugating a detection enzyme to the avidin, for example horseradish peroxidase, the presence of the target analyte is determined. For this immunohistochemical assay format, the quality control reagents may comprise: (1) the antigen or epitope bound by the primary antibody; (2) a serum fraction, an antibody fraction, or substantially purified antibodies containing the same isotype antibodies as the primary antibody and which is obtained from the same species from which the primary antibody was generated, (3) avidin conjugated to an inert carrier, preferably an inert protein carrier, e.g., bovine serum albumin, or conjugated to the substrate via chemical linkers, and (4) horseradish peroxidase conjugated to an inert carrier protein, or conjugated to the substrate via chemical linkers. Because many immunohistochemical assays are carried out on microscope slides, a dilution series of the quality control compounds are attached to a microscope slide at spatially defined sites. The horseradish peroxidase activity is readily detected using known substrates (e.g., diaminobenzidine). Performing the immunohistochemical assay on the device and detecting the signal from horseradish peroxidase activity gives an indication of the quality of reagents, and validation of assay performance. Differences in the signal intensity generated with the various quality control compounds provide information on the particular assay steps and reagents responsible for the differences in signal generation. Variations may be introduced into the device by the skilled artisan, including, use of different antigen or epitope compounds (e.g., synthetic peptides or naturally occurring proteins); alterative inert carriers for avidin and horseradish peroxidase; and different substrates to which the reference compounds are attached.

By appropriate choice of reference compounds, a single substrate can be adapted to test more than one type of immune-based or immunohistochemical assay. For example, primary antibodies are commonly obtained from a variety of animals, particularly mammals such as mouse, rat, rabbit, guinea pig, etc. Secondary or non-primary antibodies are raised in an animal species different from the animal species from which the primary antibodies are obtained. To provide a panel of suitable reference compounds for these reagent antibodies, serum proteins from animals in which the primary and non-primary antibodies are raised may be attached to the substrate to test immuno-based assays using antibodies made in different animal species. In addition, various types of detection formats may be placed on the substrate. These include, by way of example and not limitation, inert carriers or linkers conjugated to avidin, alkaline phosphatase; horseradish peroxidase; and β-galatosidase. Consequently, a single device can be adapted for testing a myriad of immuno-based assays.

Given the guidance herein, a person skilled in the art can determine the relevant quality control compounds for the various immune-based assays known in the art, and make and use the present invention, including variations thereof by routine methods and testing. In particular, the present invention provides a specific process control for immunostaining procedures, and methods for assessing the correct assay performance of these procedures and tracking reagent quality.

In a further aspect, as described above, the binding assay may comprise a hybridization assay. The label may be added to the target nucleic acid(s) prior to, or after the hybridization. Often, the label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes, thus providing a direct label that is easily detected. For a detailed review of methods of labeling nucleic acids and detecting labeled hybridized nucleic acids see *Laboratory Techniques in Biochemistry and Molecular Biology*, Vol 24: Hybridization With Nucleic Acid Probes, P. Tijssen, ed., Elsevier, N.Y., (1993) which is hereby incorporated by reference in its entirety.

In another aspect, the assays for which quality control reagents may be used comprise an enzyme assay. By an "enzyme assay" herein refers to an assay for the presence of particular enzyme activities in the sample. Enzymes that may be detected are described above, and include any relevant enzyme. In a preferred embodiment, the enzymes detected are markers for various cells, developmental stages, and disease states. Various enzyme assay formats are known in the art. These include, but are not limited to, enzyme histochemical assay, chemiluminescent assay, and electrochemiluminescent assay. In these and other formats, the quality control reagents comprise the cognate enzymes attached to substrates, particularly solid substrates. These control compounds may be in the form of substantially purified enzymes, partially purified enzymes, or cell lysates known to contain the cognate enzyme activity and which react positively with enzyme substrates. As used herein, "cells lysates" include natural and recombinant sources, including products expressed in bacteria, yeast, insects cells, mammalian cells, plant cells, and the like.

By an "enzyme histochemical" assay" herein refers to an assay in which the enzymatic product is insoluable in the assay medium, thus forming a detectable precipitate near the spatially defined site containing the quality control reagent. Exemplary enzymes for which histochemical assays are available include, but are not limited to, chymase, tryptase, carboxypeptidase and other proteases (e.g., using aminoacyl or peptidyl derivatives of 4-methoxy-2-naphthylamide; Gersch, C. et al., *Hitochem Cell Biol*. 118:41-49 (2002)); gamma-glutamyl transpeptidase; cytochrome C oxidase (CCO); succinate dehydrogenase (SDH); nicotinamide adenine phosphate dinucleotide (reduced form)-dehydrogenase (NADPH-DH); nitric oxide synthase; acetylcholinesterase (AChE); dipeptidyl peptidase IV; peroxidases, such as myeloperoxidase and horseradish peroxidase; NADPH-diaphorase; 5'-nucleotidase; alkaline phosphatase; glutathione S-transferase; catalase; glucose-6-phosphatase; aminopeptidase; guanylate cyclase; glycogen phosphorylase; aminopeptidase M (APM); glycyl-proline-MNA for dipeptidyl peptidase IV (DPP IV), lysyl-proline-MNA and lysyl-alanine-MNA for dipeptidyl peptidase II (DPP II), glycyl-arginine-MNA for dipeptidyl peptidase I (DPP I); carbobenzoxy (CBZ)-arginyl-arginine-MNA for cathepsin B; protein-tyrosine phosphatase; UDP-glucuronosyl-transferase; glucose oxidase, etc.

By "enzyme chemiluminescent assay" herein refers to an assay in which light is released from a chemical reaction involving an oxidized species generated by enzymatic activity. Basis of chemiluminescent assays, include, but are not limited to, peroxyoxalate chemiluminescence, luminol chemiluminescence, and 1,2-dioxetene substrates. In peroxyoxalate systems, an oxidant such as hydrogen peroxide reacts with peroxyoxalates (e.g., bis(2,4,6-trichlorophenyl) oxalate: TPCO) to produce an intermediate 1,2-dioxetanedione, which excites a fluorophore. In luminol based systems, an oxidant reacts with luminol or luminol derivatives (e.g., isoluminol) in the presence of a catalyst to generate a light emitting species. In 1,2-dioxetane systems, an enzyme acts on a dioxetane derivative resulting in a metastable intermediate, which upon cleavage emits light. Exemplary enzymes detectable by chemiluminescence include, among others, peroxidases, oxidases (e.g., glucose oxidase, xanthine oxidase, etc.), superoxide dismutase, phosphatases (e.g., alkaline phosphatase, etc.), glycosidases, and the like.

By "enzyme electrochemiluminescent assay" or "electrogenerated chemiluminescence" herein refers to assays based on electrogenerated chemical reaction resulting in an excited chemical compound that emits light upon decay to the resting state (Bard, A. J. and Faulkner, L. R., *Electrochemical Methods: Fundamentals and Applications*, 2nd Ed., John Wiley, New York, N.Y. (2001): hereby incorporated by reference). Enzymes assays using electrochemiluminescence may be based on substrates containing metal-ligand complexes which upon enzymatic catalysis bind to nonelectrochemiluminescent complex ruthenium (II) bis(bipyridyl), Ru(bpy)2(2+) to form electrochemiluminescent mixed-ligand complexes. Esterase, aminopeptidase, and lactamase activities have been measured (Dong, L. et al., *Anal Biochem*. 236(2):344-7 (1996); Liang, P., *Anal Chem*. 68(14): 2426-31 Another electrochemiluminescent enzyme assay uses luminol and is suitable for detecting activity of oxidases (Marquette, C. A., *Luminescence* 16(2):159-165 (2001); Wilson, R. et al. *Analyst* 128(5):480-485 (2003)).

Another type of assay useful for the present invention are assays in which an enzyme is used to chemically modify a target analyte in the sample, with subsequent detection of the chemical modification. The chemical modification may be based on reactive functional groups; photoactive groups; or coordination chemistry, generally involving covalent modification. Various assays for detecting the presence of target analytes by covalent modifications are known. For example, primary and secondary amines, such as terminal and lysine amino acids, react with dansyl chloride, ninhydrin, or fluorescamine to generate a detectable product. A quality control compound for such an assay will include known proteins with reactive amino groups, or various amino acids. Other types of detection reactions are well known to the skilled artisan.

In another aspect, the chemical modification is through use of an enzyme that modifies the target analyte in the sample with subsequent detection of the modification. Various such assays are known in the art. For instance, TUNEL assay measures DNA fragmentation appearing in apoptotic cells by labeling the 3'-hydroxyl termini of DNA fragments with the enzyme terminal deoxynucleotidyl transferase (TdT) in presence of a modified deoxyuridine triphosphate. Incorporation of bromo-dUTP (BrdU) or digoxigenin-dUTP is detected with antibodies directed to the modified nucleotide or ligand, while dUTP modified with biotin is detected using labeled avidin/streptavidin. Alternatively, the dUTP has a directly detectable label, such as a fluorescent moiety. In one embodiment, if bromo-dexoyuridine is the dUTP and detection is with avidin labeled antibodies, the quality control compounds for such an assay comprises (1) suitably fragmented DNA, (2) DNA which does not serve as TdT substrates but which contains BrdU (e.g., synthetic DNA with dideoxy-terminal ends), (4) avidin conjugated to an inert carrier, and (5) detection enzyme conjugated to a carrier. This configuration provides quality controls for the TdT enzyme activity, antibody reagent directed to BrdU, avidin/streptavidin reagent, and the detection enzyme conjugated to avidin/streptavidin.

Other embodiments of enzymatic chemical modification of a target analyte are polymerase assays, particularly in situ polymerase assays, including in situ polymerase chain reaction. In these methods, a sample on a substrate is contacted with a polymerase, preferably in presence of a primer, which may or may not be sequence specific. Extension of primers hybridized to nucleic acids in the presence of labeled nucleotides results in generation of labeled nucleic acids. Non-specific or specific nucleic acids are detectable. When coupled to polymerase chain reaction conditions, specific nucleic acids are amplified in situ, which can be localized to cells or tissues. Such in situ polymerase reactions may be used to detect specific RNA and DNA sequences (Stamps, A. C. et al., *J Nanobiotechnology* 1:3 (2003); Mitra, R. D., *Nucleic Acids Res.* 27(24):e34 (1999); Teo, I. A. et al. *Histochem. J.* 27:647-659 (1995); publications hereby incorporated by reference).

In a further aspect, the assay comprises a "histochemical stain assay" in which target analytes or structures, including those of cells and tissues, are stained by a histochemical stain, as provide in detail above (*Conn's Biological Stains*, (Horobin, R. W. and Kiernan, J. A. ed.) 10th Ed., Biological Stain Commission, BIOS Scientific Publishers, Oxford, UK (2002); Haugland, R. P., "*Handbook of Fluorescent Probes and Research Products*," 6th Ed., Molecular Probes, Eugene Oreg., (2002); Kiernan, J. A., "*Histological and Histochemical Methods: Theory and Practice*," 3$^{rd}$ Ed., Oxford, UK (2000)). Histochemical and histological stains are known in the art for purposes of staining blood and lymphocytes, connective tissue, nucleic acids, carbohydrates, lipids, inorganic ions, small molecule organic compounds; and the like. Exemplary histochemical staining assays include, by way of example and not limitation, identification of mast cells by toluidine blue and alcian blue/safranin dyes (Valchanov, K. P. and Proctor, G. B., *J. Histochem. Cytochem.* 47:617-622 (1999); identification of lipids by oxidation with osmium tetraoxide; identification of nuclei and extranuclear RNA by staining with cresyl violet; mitochondrial and oxidative enzyme staining with nitro blue tetrazolium (NBT); nuclear and glycogen staining with hematoxylin-eosin; blood cell staining with thiazine-eosinate dyes (i.e., Romanowsky-Giemsa stains); cutin, chromatin, lignin, phenol and tannin staining with safranin red; and lignin staining with phloroglucinol.

It is to be understood that an "assay" is not limited to the specific types of assay described above, nor that "assay" is limited to a single type of assay. Combinations of different assay types may be used for the present invention. These include various combinations of immuno-based assays; enzyme assays; histochemical stain assays; hybridization assays, etc. For example, an immunohistochemical assay may be combined with a histochemical stain to identify not only the target analyte but also reveal other cellular structures and/or provide counter stain for enhanced visualization of the immunohistochemical signal.

Upon performance of the assay, assessing the extent of reaction between the quality control compounds and reagents is done by various methods known in the art, depending on the nature of the reaction. These methods generally rely on generation of a detectable signal. The detectable signal includes, but are not limited to, radioactivity, absorbance, transmittance, light scattering, fluorescence, chemiluminescence, electrochemiluminescence, conductivity, etc. Included within "detectable signal" is quenching or interference with a positive signal to produce a decrease in the positive signal, or alternatively, energy transfer techniques such as fluorescence energy transfer (FRET). A decrease in a detectable signal arises in cases such as fluorescence quenching or color quenching where presence of a compound interferes with the absorbance or fluorescence emission of a fluorophore or chromophore. An interfering compound may be the reagent or reference compound. FRET signals arise when there is transfer of energy from a donor fluorophore to an acceptor fluorophore as a result of a dipolar coupling of their transition dipoles (i.e., Förster mechanism). As with quenching systems, the first fluorophore in a FRET system may comprise the reagent while the second fluorophore comprises the reference compound, or vice versa. These and other detectable signal systems may be used in the present invention.

As described herein, reagents themselves may comprise a directly detectable signal or form a detectable product upon reaction with the quality control compound, and thus provide the basis for assessing extent of the reaction. In other embodiments, the reagent contains a label moiety or a ligand which is detected. In yet a further embodiment, the reaction product is detected by a detection probe specific for the product or the reagent. These include probes which specifically interact with the reagent or product, including, but not limited to, histochemical stains, ligand/binding partner combinations, antibodies, reaction with functional groups in the product; and the like. It is to be noted that in certain embodiments, the reagents used in an assay and basis for detecting the interaction of reagent and reference compounds are the same.

In one aspect, the reaction is detected using a label moiety. The label may be a direct label or an indirect label. By "direct label" herein refers to labels that are directly detectable or produces a detectable signal. Suitable direct labels include radiolabels, fluorophores, chromophores, chelating agents, chemiluminescent moieties, electrochemiluminescent compounds, electron transfer moieties, etc. Suitable radiolabels include, without limitation, $^3$H, $^{14}$C, $^{32}$P, $^{35}$S, $^{57}$Co, $^{125}$I, and $^{131}$I. Among examples of chromophores and colored labels include, without limitation, metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); dyes encapsulated in liposomes as described by Campbell et al. (U.S. Pat. No. 4,703,017); and stain compounds described above (Horobin, supra). Suitable fluorophores include, without limitation, fluorescein, rhodamine, phyoerythrin, Texas red, Tritc C, ethidium bromide, chelated ruthenium and lanthanide complexes, and fluorescent proteins (e.g., Matz, M. V. et al., *Nat Biotechnol.* 17(10):969-73 (1999); Tsien, R. Y., *Annu. Rev. Biochem.* 67:509-544 (1998)). Suitable chemiluminescent moieties include, without limitation, acridan compounds (U.S. Pat. No. 5,750,698; 5,523,212; 5,723,295); anthryl compounds, imidazopyrazinone derivatives (Shimomura, O., *Anal Biochem.* 258(2): 230-235 (1998)); biacridylidenes (Papadopoulos, J. et al., *Anal. Chim. Acta.* 304:91 (1995)); acridinium esters; anthracene derivatives; (McCapra and Beheshti, *Bioluminescence and Chemiluminescence: Instruments and Applications*, K Van Dyke ed., CRC Press, Boca Raton, Fla. (1985)). Suitable electrochemiluminescent compounds or moiety may comprise a metal-containing organic compound wherein the metal is selected from the group consisting of ruthenium, osmium, rhenium, iridium, rhodium, platinum, palladium, molybdenum and technetium. In one preferred embodiment, the metal is ruthenium, rhenium or osmium. Exemplary ruthenium complexes include, by way of example and not limitation, tris(2,2'-bipyridine)ruthenium (II) (Blackburn, G. et al. *Clin. Chem.* 37, 1534-1539 (1991); bis[(4,4'-carbomethoxy)-2,2'-bipyridine]2-[3-(4-methyl-2,2'-bipyridine-4-yl)propyl]-1,3-dioxolane ruthenium (II); bis (2,2'bipyridine) [4-(butan-1-al)-4'-methyl-2,2'-bipyridine] ruthenium (II); and (2,2'-bipyridine)[cis-bis(1,2-diphenylphosphino)ethylenel]{2-[3-(4-methyl-2,2'-bipyridine-4'yl)propyl]-1,3-dioxolane}osmium (II). Exemplary rhenium-ligand complexes are described in U.S. Pat. No. 6,468,741; hereby incorporated by reference. Other types of electrochemical compounds may be based on rubrene, or anthracene derivatives, such as 9,10-diphenylanthracene and 9,10-dimethylanthracene dimers. Other direct labels suitable as a detectable label will be apparent to those skilled in the art.

In addition to these direct labels, the label may comprise an indirect label. By "indirect" label herein refers to a label that produces a detectable signal in presence of another molecule. Suitable indirect labels include, but are not limited to, enzymes capable of interacting with a substrate to produce a detectable signal, ligand capable of binding a binding partner containing label moieties, and the like. Types of enzyme of interest are detection enzymes, which will primarily be hydrolases, particularly phosphatases, esterases and glycosidases, or oxidoreductases, as provided in detail herein. Exemplary enzymes include β-galactosidase, horseradish peroxidase, alkaline phosphatase, glucose oxidase, β-glucouronidase, urease, glucose-6-phosphate dehydrogenase, and lactate dehydrogenase, and the like. Suitable ligand and labeled binding partner combinations include, by way of example and not limitation, biotin and avidin/streptavidin; chitin and chitin binding protein; antigen/hapten and antibody; cholesterol and cholesterol binding compounds digitonin, tomatine, filipin, and amphotericin B; ligands and cognate receptors; enzyme and enzyme inhibitors; and the like.

The signal is detected by a variety of methods depending on the type of label and detectable signal. Radioactivity based labels are detectable with photographic emulsion, placed directly on the substrate or juxtaposed to the substrate surface (i.e., autoradiography), or use of indirect signal detection using radioactivity initiated luminescence (e.g., phosphorimagers). For chromophore and chromagens absorbing a particular electromagnetic radiation spectrum, assessments may be done visually or by measuring absorbance or transmittance. Scanning densitometers are commercially available for such purposes. Signals based on fluorescence are detected by exciting the molecule with light in the fluor's excitation spectrum and detecting photon emission in the emission spectrum. Devices useful for fluorescence measurement include fluorimagers, particularly multicolor imagers (see, e.g., Molecular Dynamics); fluorescence and scanning fluorescence microscopes; etc. Signals based on chemiluminescence are measured similar to fluorescence, except that the emission is measured. Chemiluminescence is measured with any light-sensing device capable of detecting photo signals in the emission spectrum, including without limitation, photomultiplier tubes, charge coupled devices (CCD), and complementary metal oxide semiconductor (CMOS) devices. Electrochemiluminescence is initiated by applying a electrical potential across the reaction product and the detecting the resulting emission of light as done for chemiluminescence.

In some embodiments, particularly where the detectable signal is a chromogenic particle, particularly insoluble products of a detection enzyme, the assessments of the reaction may be made by measuring light scattering. The light may be directed through the substrate, if optically transparent, or illuminated onto the substrate surface, and the resulting light scattered by the particulate matter measured. Use of a photomultiplier tube, CCD device, or CMOS device to collect the light signal and its conversion into a digital readout provides a quantitative basis to assess the reaction. Analysis of digital readouts via pixel counting is a generally applicable method for any type of photometric technique.

The present invention also relates to kits containing the devices described herein. In one aspect, the kit comprises the device of the present invention and related instructions on methods of using the device. The instructions may be on any format, including, but not limited to, printed medium, video, computer readable medium (e.g., compact disc, magnetic disc, etc.), and the like. The kit may contain assay reagents for performing an assay, particularly an immunohistochemical assay, which may be used as a set of control reagents for testing and comparing assays carried out on samples. The device may also be part of target analyte detection kits, particularly immunohistochemical assay kits. These and other embodiments are encompassed by the present invention.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

All patents, patent applications, publications, and references cited herein are expressly incorporated by reference to the same extent as if each individual publication or patent application was specifically and individually indicated to be incorporated by reference.

EXAMPLES

Example 1

A glass microscope slide was cleaned with detergent and alcohol, and subsequently coated with aminoalkylsilane (1% solution in 95% ethanol for 10 min or 1 hr.). Serum proteins from mouse, rabbit, sheep, rat and guinea pig are applied to the derivatized substrate surface at spatially defined sites using a micropipette. Additional reference compounds comprise horse serum proteins conjugated to biotin, horseradish peroxidase, or alkaline phosphatase. Each reference compound is present as a graded dilution series from 100% (i.e., about 60 mg protein/ml), 50%, 25%, 12.5% and 6.25%. Although the spots may be larger or smaller, depending on the detection method, they are generally about 250 um to permit visual inspection of the results. Optionally, formaldehyde was used to further conjugate the quality control compounds to the glass substrate.

The quality control slide is processed in an immunhistochemical assay, preferably after the steps in which the experimental slides containing the samples have been deparaffinized and hydrated. Thereafter, the quality control slides are processed the same as the sample slides. After final chromogen development, slides are rinsed, and if permissible, dehydrated. Generally, these slides are not counterstained with a histochemical stain since inclusion of such stains may complicate visual inspection.

Positive staining should be seen in each species row for which the immunohistochemical staining is sensitive. A row of a species serum protein should not produce a signal if the immunohistochemical staining procedure does not have specific antisera directed to that particular animal species, unless there is some non-specific species cross reactivity of the antibodies.

If the immunohistochemical staining procedure is based on biotin-avidin/streptavidin, positive staining should be seen in the biotin containing row. Analogously, for a peroxidase enzyme detection system, positive staining should be seen in the peroxidase row, while for an alkaline phosphatase system, positive staining should be present in the alkaline phosphatase row. It is to be understood that the quality control devices of the present invention is adaptable to multiple detection systems as well as to single detection systems. By way of example and not limitation, a immunohistochemical assay directed to detecting multiple target analytes in a single sample (e.g., "multicolor assays") may use an alkaline phosphatase detection for one target analyte and a horseradish peroxidase detection for the second target analyte. Quality control assessments of both systems are possible with the described device if distinguishable enzyme detection systems are used.

What is claimed:

1. A device for determining quality of a reagent used in an assay, comprising:
   a) a target of a secondary antibody to be used in said assay; said target being bound on a first plurality of spatially defined sites an a substrate, and each of said first plurality of spatially defined sites having a different amount of said target;
   b) a secondary antibody conjugate comprising said secondary antibody and a ligand to be used in said assay; said secondary antibody conjugate being bound by a first linking moiety on a second plurality of spatially defined sites on said substrate, each of said second plurality of spatially defined sites having a different amount of said secondary antibody conjugate; and
   c) an enzyme conjugate comprising an enzyme to be used in said assay and a binding partner specific to said ligand; said enzyme conjugate being bound by a second linking moiety on a third plurality of spatially defined sites on said substrate, each of said third plurality of spatially defined sites having a different amount of said enzyme conjugate.

2. The device of claim 1, wherein said target of said secondary antibody is a serum protein of an animal species.

3. The device of claim 2, wherein said species is one selected from the group consisting of bovine, cat, chicken, dog, donkey, goat, guinea pig, hamster, horse, human, mouse, rabbit, rat, sheep, and swine.

4. The device of claim 1, wherein said linking moiety comprises crosslinking agent, peptide, protein, nucleic acid or carbohydrate.

5. The device of claim 4, wherein said linking moiety is a horse serum protein.

6. The device of claim 4, wherein said protein of said linking moiety is different from said secondary antibody used in said assay.

7. The device of claim 1, wherein said binding partner is avidin, or streptavidin.

8. The device of claim 1, wherein said enzyme conjugate comprises horseradish peroxidase, or alkaline phosphatase.

9. The device of claim 1, wherein said enzyme conjugate comprises β-galactosidase, glucose oxidase, β-glucouronidase, urease, glucose-6-phosphate dehydrogenase, or lactate dehydrogenase.

10. The device of claim 1, wherein said different amount is a serial dilution series of said target, said secondary antibody conjugate, or said enzyme conjugate.

11. The device of claim 1, wherein said substrate comprises aminoalkylsilane.

12. The device of claim 1, wherein said substrate is attached to a solid support.

13. The device of claim 12, wherein said solid support comprises a microscope slide.

14. The device of claim 1, wherein said device contains an identifying code.

15. The device of claim 1, wherein said assay comprises an immuno-based assay.

16. The device of claim 1, wherein said assay comprises an immunohistochemical assay.

* * * * *